(12) United States Patent
Krammer et al.

(10) Patent No.: US 6,770,474 B2
(45) Date of Patent: Aug. 3, 2004

(54) P53 BINDING AREAS

(75) Inventors: Peter Krammer, Heidelberg (DE); Martina Muller-Schilling, Heidelberg (DE); Moshe Oren, Rehovot (IL)

(73) Assignee: Deutsches Krebsforschungszentrum, Heidelberg (DE)

(*) Notice: Subject to any disclaimer, the term of this patent is extended or adjusted under 35 U.S.C. 154(b) by 0 days.

(21) Appl. No.: 09/834,291

(22) Filed: Apr. 12, 2001

(65) Prior Publication Data

US 2002/0042064 A1 Apr. 11, 2002

Related U.S. Application Data

(63) Continuation of application No. PCT/DE99/03343, filed on Oct. 18, 1999.

(30) Foreign Application Priority Data

Oct. 16, 1998 (DE) .......................................... 198 47 779

(51) Int. Cl.$^7$ ........................ C12N 15/63; C07H 21/04; C12Q 1/68
(52) U.S. Cl. ........................ 435/320.1; 536/24.1; 435/6
(58) Field of Search ...................... 536/24.1; 435/320.1, 435/6

(56) References Cited

FOREIGN PATENT DOCUMENTS

| EP | 0 518 650 | 6/1992 |
|---|---|---|
| WO | WO 95/19367 | 7/1995 |
| WO | WO 98/08965 | 3/1998 |

OTHER PUBLICATIONS

Owen–Schaub et al., Wild type human p53 and a temperature–sensitive mutant induce Fas/APO–1 expression, 1995, Molecular and Cellular Biology, P. 3032–3040.*

Tolomeo et al., The CD95/CD95 ligand system is not the major effector in anticancer drug–mediated apoptosis, 1998, Cell Death and Differentiation, vol. 5, pp. 735–742.*

Ruiz–Ruiz et al., p53–mediated up–regulation of CD95 is not involved in genotoxic drug–induced apoptosis of human breast tumor cells, 1996, Cell Death and Differentiation, vol. 6, pp. 271–280.*

Friesen et al., Cytotoxic drugs and the CD95 pathway, 1999, LEUKEMIA, vol. 13, pp. 1854–1858.*

Muller et al., p53 activates the CD95 (APO–1/Fas) gene in response to DNA damage by anticancer drugs, 1998, j. exp. med., vol. 188, pp. 2033–2045.*

Rudert et al., Identification of a silencer, enhancer, and basal promoter region in the human CD95 (Fas/APO–1) gene, 1995, DNA and Cell Biology, vol. 14, pp. 931–937.*

Fulda et al., The CD95 (APO–1/Fas) system mediates drug–induced apoptosis in neuroblastoma cells, 1997, Cancer Research, vol. 57, pp. 3823–3829.*

Behrmann, et al., "Structure of the human APO–1 gene." Eur. J. Immunol. 1994. 24: p. 3057–3062.

XP 000572417. Chan & Owen Schaub, "Identification and analysis of A p53 binding element within the promoter of the FAS/APO–1 (CD95) gene,".

XP–000906792. Muller et al., "p53 activates the CD95 (APO–1/FAS) gene in response to DNA damage by anticancer drugs," J. Exp. Med. 1998: vol. 188, No. 11. p. 2033–2045.

XP–000906826. Rudert et al., "Identification of a silencer, enhancer, and basal promoter region in the human CD95 (FAS/APO–1) gene," DNA and Cell Biol., 1995: vol. 14, No. 11, p. 931–937.

* cited by examiner

*Primary Examiner*—David Guzo
*Assistant Examiner*—Daniel M. Sullivan
(74) *Attorney, Agent, or Firm*—Marianne Fuierer; Steven J. Hultquist

(57) ABSTRACT

The present invention relates to p53 binding regions on a CD95 receptor DNA and to the application of the p53 binding regions to influence apoptosis and/or identify suitable substances therefor.

6 Claims, 26 Drawing Sheets

```
       GATCCCGCTGGGCAGGCGGGGCAGCTCCGGCGCTCCTCGGAGACCACTGCGCTCCACGTT
  1    ------------+----------+----------+----------+----------+----------+ 60
       CTAGGGCGACCCGTCCGCCCCGTCGAGGCCGCGAGGAGCCTCTGGTGACGCGAGGTGCAA

GAGGTGGGCGTGGGGGGCGGACAGGAATTGAAGCGGAAGTCTGGGAAGCTTTAGGGTCGC
  61   ------------+----------+----------+----------+----------+----------+ 120
       CTCCACCCGCACCCCCCGCCTGTCCTTAACTTCGCCTTCAGACCCTTCGAAATCCCAGCG

<---- 4.P53-BR ---->
                                                    (intron)
       TGGAGGGGGACCCCGGTTGGAGAGAGGAGCGGAACTCCTGGACAAGCCCTGACAAGCCAA
 121   ------------+----------+----------+----------+----------+----------+ 180
       ACCTCCCCCTGGGGCCAACCTCTCTCCTCGCCTTGAGGACCTGTTCGGGACTGTTCGGTT GCCAAAGGTCCGCTCCGGCGCGGGTGGGTGAGTGCGCGCCGCCCCGCGGGGGCGGGGAGA
 181   ------------+----------+----------+----------+----------+----------+ 240
       CGGTTTCCAGGCGAGGCCGCGCCCACCCACTCACGCGCGGCGGGGCGCCCCGCCCCTCT GAGCCTACAGCCTTCAGAACACATATTGCTCATTTTCTGGCAGTTCTCAGACGTAGGAAA
 241   ------------+----------+----------+----------+----------+----------+ 300
       CTCGGATGTCGGAAGTCTTGTGTATAACGAGTAAAAGACCGTCAAGAGTCTGCATCCTTT TAAGTCAGCACCGAAGCAGTGGTTAAGCCGGAGGGCTCGGAAGAACGGCACCTTTTCTTT
 301   ------------+----------+----------+----------+----------+----------+ 360
       ATTCAGTCGTGGCTTCGTCACCAATTCGGCCTCCCGAGCCTTCTTGCCGTGGAAAAGAAA CTCGAAAAAGTTATATGGGGGCTGAATGAGCTTCTGGAGGCTTGTTTACCGTTTTTTATT
 361   ------------+----------+----------+----------+----------+----------+ 420
       GAGCTTTTTCAATATACCCCCGACTTACTCGAAGACCTCCGAACAAATGGCAAAAAATAA GTCACACAGAAAAGGAAACTGCCTTGTCTCCCTTCCGGGAATTCTCTCTTTAAGACTGTA
 421   ------------+----------+----------+----------+----------+----------+ 480
       CAGTGTGTCTTTTCCTTTGACGGAACAGAGGGAAGGCCCTTAAGAGAGAAATTCTGACAT AGTCGCTGCCTGAGTGGTTTCATTTTGTTTTGTTTTTCTGCCCTTCTCTTTCTTCTTTTG
 481   ------------+----------+----------+----------+----------+----------+ 540
       TCAGCGACGGACTCACCAAAGTAAAACAAAACAAAAAGACGGGAAGAGAAAGAAGAAAAC CCCTTTCTTAGCTTGCACTCCCATGGTGATTTCTGCTTGGTCTCCTGCTGGGGTTGGTGG
 541   ------------+----------+----------+----------+----------+----------+ 600
       GGGAAAGAATCGAACGTGAGGGTACCACTAAAGACGAACCAGAGGACGACCCCAACCACC TACTCGTTCCCACCGCACAGAACCCGGCGCCTATTATTGGCCAAGAAACTTGAGCAGCCT
 601   ------------+----------+----------+----------+----------+----------+ 660
       ATGAGCAAGGGTGGCGTGTCTTGGGCCGCGGATAATAACCGGTTCTTTGAACTCGTCGGA GTTTTGAAAAGTCCCTCGCTCAGAAATGCCAGCTTGCAGATGGCTAATCAAAGAGACGTG
 661   ------------+----------+----------+----------+----------+----------+ 720
       CAAAACTTTTCAGGGAGCGAGTCTTTACGGTCGAACGTCTACCGATTAGTTTCTCTGCAC
```

Fig. 7

2nd half of the
2.p53-BE
(promoter)

```
                      AGCTTTTTTGGCTACATTTTTTTATTTGTAAAG
           448  ---+----------+----------+---------+  480
                      TCGAAAAAACCGATGTAAAAAAATAAACATTTC

TAAGTTTAATAATCACTCATCTCACTGGGCTATAATGATAAGTATTAAGTAAGGAAGATC
           481  ----------+----------+----------+----------+----------+---------+  540
                ATTCAAATTATTAGTGAGTAGAGTGACCCGATATTACTATTCATAATTCATTCCTTCTAG

CACATATGTGAGTTGCTGGCTTATAATTCACACTCAAGAGATACTGATTTTGTCAATTGT
           541  ---------+----------+----------+----------+----------+---------+  600
                GTGTATACACTCAACGACCGAATATTAAGTGTGAGTTCTCTATGACTAAAACAGTTAACA

CCTTTCCCCTTTTTTTCTCTCTTCCCTCCTTCCATTCCTTCTTCCCTTACCTCTCCTTTC
           601  ----------+----------+----------+----------+----------+---------+  660
                GGAAAGGGGAAAAAAAGAGAGAAGGGAGGAAGGTAAGGAAGAAGGGAATGGAGAGGAAAG

CTTCCCTCACACCCCTTTTCCTTCCTTCTTTTTACATTTTTTTATTTAAATGAACTTTTC
           661  ----------+----------+----------+----------+----------+---------+  720
                GAAGGGAGTGTGGGGAAAAGGAAGGAAGAAAAATGTAAAAAAATAAATTTACTTGAAAAG

ATTTTGGAATAGTTTTAGGATTTCAAAAAATTTGCAGAGATAATACAGAGAATGCCCATA
           721  ----------+----------+----------+----------+----------+---------+  780
                TAAAACCTTATCAAAATCCTAAAGTTTTTTAAACGTCTCTATTATGTCTCTTACGGGTAT

TACCATCCTCCTTATCCCACTTCTTTTTGTGTCTATTAGATGCTCAGAGTGTGTGCACAA
           781  ----------+----------+----------+----------+----------+---------+  840
                ATGGTAGGAGGAATAGGGTGAAGAAAAACACAGATAATCTACGAGTCTCACACACGTGTT

GGCTGGCACGCCCAGGGTCTTCCTCATGGCACTAACAGTCTACTGAAAGGTGGAACAGAG
           841  ----------+----------+----------+----------+----------+---------+  900
                CCGACCGTGCGGGTCCCAGAAGGAGTACCGTGATTGTCAGATGACTTTCCACCTTGTCTC

ACAAGCCTATCAACACCTACAAGACTGGTGGTAAGTGCAGTGACAGATGCAAAACACAGG
           901  ----------+----------+----------+----------+----------+---------+  960
                TGTTCGGATAGTTGTGGATGTTCTGACCACCATTCACGTCACTGTCTACGTTTTGTGTCC

GTGATGGAAAGCCCTCAGGAGGGTAACCTAACCTAGATTTGAGGGCCCAAACAGGCTCCA
           991  ----------+----------+----------+----------+----------+---------+  1020
                CACTACCTTTCGGGAGTCCTCCCATTGGATTGGATCTAAACTCCCGGGTTTGTCCGAGGT

GAAGAAAATGTCAACTGAGAGGAAGCCTGAAGGATGAACAGTGGGCTAAGCAAAGGGTTA
           1021 ----------+----------+----------+----------+----------+---------+  1080
                CTTCTTTTACAGTTGACTCTCCTTCGGACTTCCTACTTGTCACCCGATTCGTTTCCCAAT
```

Fig. 8A

```
              TTAATGTGTTATTAATGGGTTGAATCTAATTGGGAAGGGAGAGAGGTTGCAGAGTGAGGT
1081     ---------+---------+---------+---------+---------+---------+   1140
              AATTACACAATAATTACCCAACTTAGATTAACCCTTCCCTCTCTCCAACGTCTCACTCCA

GCAGAGCTTGGTGGACGATGCCAAAGGAATACTGAAACCTTTAGTGTGTCCAGTCTGGAA
1141     ---------+---------+---------+---------+---------+---------+   1200
              CGTCTCGAACCACCTGCTACGGTTTCCTTATGACTTTGGAAATCACACAGGTCAGACCTT

CTGCATCCAAATTCAGGTTCAGTAATGATGTCATTATCCAAACATACCTTCTGTAAAATT
1201     ---------+---------+---------+---------+---------+---------+   1260
              GACGTAGGTTTAAGTCCAAGTCATTACTACAGTAATAGGTTTGTATGGAAGACATTTTAA

←--- 3.p53-B2 ---→
                         (promoter)

CATGCTAAACTACCTAAGAGCTATCTACCGTTCCAAAGCAATAGTGACTTTGAACAGTGT
1261     ---------+---------+---------+---------+---------+---------+   1320
              GTACGATTTGATGGATTCTCGATAGATGGCAAGGTTTCGTTATCACTGAAACTTGTCACA

TCACCAGAGCACGAAAGAATTACAAGATTTTTTTTTAAAGAAAATTGGCCAGGAAATAAT
1321     ---------+---------+---------+---------+---------+---------+   1380
              AGTGGTCTCGTGCTTTCTTAATGTTCTAAAAAAAAATTTCTTTTAACCGGTCCTTTATTA

GAGTAACGAAGGACAGGAAGTAATTGTGAATGTTTAATATAGCTGGGGCTATGCGATTTG
1381     ---------+---------+---------+---------+---------+---------+   1440
              CTCATTGCTTCCTGTCCTTCATTAACACTTACAAATTATATCGACCCCGATACGCTAAAC

GCTTAAGTTGTTAGCTTTGTTTTCCTCTTGAGAAATAAAAACTAAGGGGCCCTCCCTTTT
1441     ---------+---------+---------+---------+---------+---------+   1500
              CGAATTCAACAATCGAAACAAAAGGAGAACTCTTTATTTTTGATTCCCCGGGAGGGAAAA

CAGAGCCCTATGGCGCAACATCTGTACTTTTTCATATGGTTAACTGTCCATTCCAGGAAC
1501     ---------+---------+---------+---------+---------+---------+   1560
              GTCTCGGGATACCGCGTTGTAGACATGAAAAAGTATACCAATTGACAGGTAAGGTCCTTG

GTCTGTGAGCCTCTCATGTTGCAGCCACAACATGGACAGCCCAGTCAAATGCCCCGCAAG
1561     ---------+---------+---------+---------+---------+---------+   1620
              CAGACACTCGGAGAGTACAACGTCGGTGTTGTACCTGTCGGGTCAGTTTACGGGGCGTTC

TCTTTCTCTGAGTGACTCCAGCAATTAGCCAAGGCTCCTGTACCCAGGCAGGACCTCTGC
1621     ---------+---------+---------+---------+---------+---------+   1680
              AGAAAGAGACTCACTGAGGTCGTTAATCGGTTCCGAGGACATGGGTCCGTCCTGGAGACG

GCTCTGAGCTCCATTCTCCTTCAAGACCTCCCCAACTTCCCAGGTTGAACTACAGCAGAA
1681     ---------+---------+---------+---------+---------+---------+   1740
              CGAGACTCGAGGTAAGAGGAAGTTCTGGAGGGGTTGAAGGGTCCAACTTGATGTCGTCTT

GCCTTTAGAAAGGGCAGGAGGCCGGCTCTCGAGGTCCTCACCTGAAGTGAGCATGCCAGC
1741     ---------+---------+---------+---------+---------+---------+   1800
              CGGAAATCTTTCCCGTCCTCCGGCCGAGAGCTCCAGGAGTGGACTTCACTCGTACGGTCG

CACTGCAGGAACGCCCCGGGACAGGAATGCCCATTTGTGCAACGAACCCTGACTCCTTCC
1801     ---------+---------+---------+---------+---------+---------+   1860
              GTGACGTCCTTGCGGGGCCCTGTCCTTACGGGTAAACACGTTGCTTGGGACTGAGGAAGG

TCACCCTGACTTCTCCCCCTCCCTACCCGCGCGCAGGCCAAGTTGCTGAATCAATGGAGC
1861     ---------+---------+---------+---------+---------+---------+   1920
              AGTGGGACTGAAGAGGGGGAGGGATGGGCGCGCGTCCGGTTCAACGACTTAGTTACCTCG
```

Fig. 8B

```
            CCTCCCCAACCCGGGCGTTCCCCAGCGAGGCTTCCTTCCCATCCTCCTGACCACCGGGGC
1921    ----------+----------+----------+----------+----------+----------+  1980
            GGAGGGGTTGGGCCCGCAAGGGGTCGCTCCGAAGGAAGGGTAGGAGGACTGGTGGCCCCG

TTTTCGTGAGCTCGTCTCTGATCTCGCGCAAGAGTGACACACAGGTGTTCAAAGACGCTT
1981    ----------+----------+----------+----------+----------+----------+  2040
            AAAAGCACTCGAGCAGAGACTAGAGCGCGTTCTCACTGTGTGTCCACAAGTTTCTGCGAA

CTGGGGAGTGAGGGAAGCGGTTTACGAGTGACTTGGCTGGAGCCTCAGGGGCGGGCACTG
2041    ----------+----------+----------+----------+----------+----------+  2100
            GACCCCTCACTCCCTTCGCCAAATGCTCACTGAACCGACCTCGGAGTCCCCGCCCGTGAC

GCACGGAACACACCCTGAGGCCAGCCCTGGCTGCCCAGGCGGAGCTGCCTCTTCTCCCGC
2101    ----------+----------+----------+----------+----------+----------+  2160
            CGTGCCTTGTGTGGGACTCCGGTCGGGACCGACGGGTCCGCCTCGACGGAGAAGAGGGCG

GGACATGTACAGAGCTCGAGAAGTACTAGTGGCCACGTGGGCCGTGCACCTTAAGCTTTA
2161    ----------+----------+----------+----------+----------+----------+  2220
            CCTGTACATGTCTCGAGCTCTTCATGATCACCGGTGCACCCGGCACGTGGAATTCGAAAT

←---4.p53-BS-
                                                    (intron)

GGGTCGCTGGAGGGGGACCCCGGTTGGAGAGAGGAGCGGAACTCCTGGACAAGCCCTGAC
2221    ----------+----------+----------+----------+----------+----------+  2280
            CCCAGCGACCTCCCCCTGGGGCCAACCTCTCTCCTCGCCTTGAGGACCTGTTCGGGACTG

---→
            AAGCCAAGCCAAAGGTCCGCTCCGGCGCGGGTGGGTGAGTGCGCGCCGCCCCGCGGGGGC
2281    ----------+----------+----------+----------+----------+----------+  2340
            TTCGGTTCGGTTTCCAGGCGAGGCCGCGCCCACCCACTCACGCGCGGCGGGGCGCCCCCG

GGGGAGAGAGCCTGCAGCCTTCAGAACAGATATTGCTCATTTTCTGGCAGTTCTCAGACG
2341    ----------+----------+----------+----------+----------+----------+  2400
            CCCCTCTCTCGGACGTCGGAAGTCTTGTCTATAACGAGTAAAAGACCGTCAAGAGTCTGC

TAGGAAATAAGTCAGCACCGAAGCAGTGGTTAAGCCGGAGGGCTCGGAAGAACGGCACCT
2401    ----------+----------+----------+----------+----------+----------+  2460
            ATCCTTTATTCAGTCGTGGCTTCGTCACCAATTCGGCCTCCCGAGCCTTCTTGCCGTGGA

TTTCTTTCTCGAAAAAGTTATATGGGGGCTGAATGAGCTTCTGGAGGCTTGTTTACCGTT
2461    ----------+----------+----------+----------+----------+----------+  2520
            AAAGAAAGAGCTTTTTCAATATACCCCCGACTTACTCGAAGACCTCCGAACAAATGGCAA

TTTTATTGTCACACAGAAAAGGAAACTGCCTTGTCTCCCTTCCGGGAATTCTCTCTTTAA
2521    ----------+----------+----------+----------+----------+----------+  2580
            AAAATAACAGTGTGTCTTTTCCTTTGACGGAACAGAGGGAAGGCCCTTAAGAGAGAAATT

GACTGTAAGTCGCTGCCTGAGTGGTTTCATTTTGTTTTGTTTTTCTGCCCTTCTCTTTCT
2581    ----------+----------+----------+----------+----------+----------+  2640
            CTGACATTCAGCGACGGACTCACCAAAGTAAAACAAAACAAAAAGACGGGAAGAGAAAGA

TCTTTTGCCCTTTCTTAGCTTGCACTCCCATGGTGATTTCTGCTTGGTCTCCTGCTGGGG
2641    ----------+----------+----------+----------+----------+----------+  2700
            AGAAAACGGGAAAGAATCGAACGTGAGGGTACCACTAAAGACGAACCAGAGGACGACCCC
```

Fig. 8C

```
     TTGGTGGTACTCGTTCCCACCGCACAGAACCCGGCGCCTATTATTGGCCAAGAAACTTGA
2701 ------------+---------+---------+---------+---------+---------+ 2760
     AACCACCATGAGCAAGGGTGGCGTGTCTTGGGCCGCGGATAATAACCGGTTCTTTGAACT

GCAGCCTGTTTTGAAAAGTCCCTCGCTCAGAAATGCCAGCTTGCAGATGGCTAATCAAAG
2761 ------------+---------+---------+---------+---------+---------+ 2820
     CGTCGGACAAAACTTTTCAGGGAGCGAGTCTTTACGGTCGAACGTCTACCGATTAGTTTC

AGACGTG
2821 ------- 2827
     TCTGCAC
```

Fig. 8D

```
                                                  <---- 1.p53-BX --
    TGAGGACTCTCAGGAATATGCTGGTAAAATAAAAATAACCTTTAGAGATGCCCAAACTGT
1   ---------+---------+---------+---------+---------+---------+ 60
    ACTCCTGAGAGTCCTTATACGACCATTTTATTTTTATTGGAAATCTCTACGGGTTTGACA

-->
    TTTCCCCAGAACACCAGCATTCATTAGGTGTTCATTCAATAGATTCTTCAAAGGATTCCA
61  ---------+---------+---------+---------+---------+---------+ 120
    AAAGGGGTCTTGTGGTCGTAAGTAATCCACAAGTAAGTTATCTAAGAAGTTTCCTAAGGT

AAGGCAAAGAAGTTTGGGGAACAGTATATATAATTACCCAACCCTTTGACATTAGCATAC
121 ---------+---------+---------+---------+---------+---------+ 180
    TTCCGTTTCTTCAAACCCCTTGTCATATATATTAATGGGTTGGGAAACTGTAATCGTATG

TAAGGGCCCTGAGAAGTTTTGGATTAAGAAAGTTTTCAAATTAAAGTAACCCAGAATTTT
181 ---------+---------+---------+---------+---------+---------+ 240
    ATTCCCGGGACTCTTCAAAACCTAATTCTTTCAAAAGTTTAATTTCATTGGGTCTTAAAA

CTAAGATTATTTGACCATGAAACATATGTCTCCCCACAAAGCACATATTCCTATCTCCTT
241 ---------+---------+---------+---------+---------+---------+ 300
    GATTCTAATAAACTGGTACTTTGTATACAGAGGGGTGTTTCGTGTATAAGGATAGAGGAA

GAACTTGAGGATAATTAGACGTACGTGGGTAGAGGGTAGGGGAAGGGGGTATGGCATAGA
301 ---------+---------+---------+---------+---------+---------+ 360
    CTTGAACTCCTATTAATCTGCATGCACCCATCTCCCATCCCCTTCCCCCATACCGTATCT

AAGAGCAGGACCTTGGGAGCAAGAATATCTAAGTTTAATTCCTGACTCTGCTATTTATTA
361 ---------+---------+---------+---------+---------+---------+ 420
    TTCTCGTCCTGGAACCCTCGTTCTTATAGATTCAAATTAAGGACTGAGACGATAAATAAT

<---- 2.p53-BE ---->
    ACTAACCATCTTTGCCAATGTTGCTTAAGCTTTTTTGGCTACATTTTTTTATTTGTAAAG
421 ---------+---------+---------+---------+---------+---------+ 480
    TGATTGGTAGAAACGGTTACAACGAATTCGAAAAAACCGATGTAAAAAAATAAACATTTC

TAAGTTTAATAATCACTCATCTCACTGGGCTATAATGATAAGTATTAAGTAAGGAAGATC
481 ---------+---------+---------+---------+---------+---------+ 540
    ATTCAAATTATTAGTGAGTAGAGTGACCCGATATTACTATTCATAATTCATTCCTTCTAG

CACATATGTGAGTTGCTGGCTTATAATTCACACTCAAGAGATACTGATTTTGTCAATTGT
541 ---------+---------+---------+---------+---------+---------+ 600
    GTGTATACACTCAACGACCGAATATTAAGTGTGAGTTCTCTATGACTAAAACAGTTAACA

CCTTTCCCCTTTTTTTCTCTCTTCCCTCCTTCCATTCCTTCTTCCCTTACCTCTCCTTTC
601 ---------+---------+---------+---------+---------+---------+ 660
    GGAAAGGGGAAAAAAAGAGAGAAGGGAGGAAGGTAAGGAAGAAGGGAATGGAGAGGAAAG
```

Fig. 9A

```
        CTTCCCTCACACCCCTTTTCCTTCCTTCTTTTTACATTTTTTTATTTAAATGAACTTTTC
661     ---------+---------+---------+---------+---------+---------+ 720
        GAAGGGAGTGTGGGGAAAAGGAAGGAAGAAAAATGTAAAAAAATAAATTTACTTGAAAAG

ATTTTGGAATAGTTTTAGGATTTCAAAAAATTTGCAGAGATAATACAGAGAATGCCCATA
721     ---------+---------+---------+---------+---------+---------+ 780
        TAAAACCTTATCAAAATCCTAAAGTTTTTTAAACGTCTCTATTATGTCTCTTACGGGTAT

TACCATCCTCCTTATCCCACTTCTTTTTGTGTCTATTAGATGCTCAGAGTGTGTGCACAA
781     ---------+---------+---------+---------+---------+---------+ 840
        ATGGTAGGAGGAATAGGGTGAAGAAAAACACAGATAATCTACGAGTCTCACACACGTGTT

GGCTGGCACGCCCAGGGTCTTCCTCATGGCACTAACAGTCTACTGAAAGGTGGAACAGAG
841     ---------+---------+---------+---------+---------+---------+ 900
        CCGACCGTGCGGGTCCCAGAAGGAGTACCGTGATTGTCAGATGACTTTCCACCTTGTCTC

ACAAGCCTATCAACACCTACAAGACTGGTGGTAAGTGCAGTGACAGATGCAAAACACAGG
901     ---------+---------+---------+---------+---------+---------+ 960
        TGTTCGGATAGTTGTGGATGTTCTGACCACCATTCACGTCACTGTCTACGTTTTGTGTCC

GTGATGGAAAGCCCTCAGGAGGGTAACCTAACCTAGATTTGAGGGCCCAAACAGGCTCCA
991     ---------+---------+---------+---------+---------+---------+ 1020
        CACTACCTTTCGGGAGTCCTCCCATTGGATTGGATCTAAACTCCCGGGTTTGTCCGAGGT

GAAGAAAATGTCAACTGAGAGGAAGCCTGAAGGATGAACAGTGGGCTAAGCAAAGGGTTA
1021    ---------+---------+---------+---------+---------+---------+ 1080
        CTTCTTTTACAGTTGACTCTCCTTCGGACTTCCTACTTGTCACCCGATTCGTTTCCCAAT

TTAATGTGTTATTAATGGGTTGAATCTAATTGGGAAGGGAGAGAGGTTGCAGAGTGAGGT
1081    ---------+---------+---------+---------+---------+---------+ 1140
        AATTACACAATAATTACCCAACTTAGATTAACCCTTCCCTCTCTCCAACGTCTCACTCCA

GCAGAGCTTGGTGGACGATGCCAAAGGAATACTGAAACCTTTAGTGTGTCCAGTCTGGAA
1141    ---------+---------+---------+---------+---------+---------+ 1200
        CGTCTCGAACCACCTGCTACGGTTTCCTTATGACTTTGGAAATCACACAGGTCAGACCTT

CTGCATCCAAATTCAGGTTCAGTAATGATGTCATTATCCAAACATACCTTCTGTAAAATT
1201    ---------+---------+---------+---------+---------+---------+ 1260
        GACGTAGGTTTAAGTCCAAGTCATTACTACAGTAATAGGTTTGTATGGAAGACATTTTAA

<---- 3.p53-B8 ---->
        CATGCTAAACTACCTAAGAGCTATCTACCGTTCCAAAGCAATAGTGACTTTGAACAGTGT
1261    ---------+---------+---------+---------+---------+---------+ 1320
        GTACGATTTGATGGATTCTCGATAGATGGCAAGGTTTCGTTATCACTGAAACTTGTCACA

TCACCAGAGCACGAAAGAATTACAAGATTTTTTTTAAAGAAAATTGGCCAGGAAATAAT
1321    ---------+---------+---------+---------+---------+---------+ 1380
        AGTGGTCTCGTGCTTTCTTAATGTTCTAAAAAAAAATTTCTTTTAACCGGTCCTTTATTA

GAGTAACGAAGGACAGGAAGTAATTGTGAATGTTTAATATAGCTGGGGCTATGCGATTTG
1381    ---------+---------+---------+---------+---------+---------+ 1440
        CTCATTGCTTCCTGTCCTTCATTAACACTTACAAATTATATCGACCCCGATACGCTAAAC

GCTTAAGTTGTTAGCTTTGTTTTCCTCTTGAGAAATAAAAACTAAGGGGCCCTCCCTTTT
1441    ---------+---------+---------+---------+---------+---------+ 1500
        CGAATTCAACAATCGAAACAAAAGGAGAACTCTTTATTTTTGATTCCCCGGGAGGGAAAA

CAGAGCCCTATGGCGCAACATCTGTACTTTTTCATATGGTTAACTGTCCATTCCAGGAAC
1501    ---------+---------+---------+---------+---------+---------+ 1560
        GTCTCGGGATACCGCGTTGTAGACATGAAAAAGTATACCAATTGACAGGTAAGGTCCTTG
```

Fig. 9B

```
            GTCTGTGAGCCTCTCATGTTGCAGCCACAACATGGACAGCCCAGTCAAATGCCCCGCAAG
1561        ------------+----------+----------+----------+----------+----------+ 1620
            CAGACACTCGGAGAGTACAACGTCGGTGTTGTACCTGTCGGGTCAGTTTACGGGCGTTC

TCTTTCTCTGAGTGACTCCAGCAATTAGCCAAGGCTCCTGTACCCAGGCAGGACCTCTGC
1621        ------------+----------+----------+----------+----------+----------+ 1680
            AGAAAGAGACTCACTGAGGTCGTTAATCGGTTCCGAGGACATGGGTCCGTCCTGGAGACG

GCTCTGAGCTCCATTCTCCTTCAAGACCTCCCCAACTTCCCAGGTTGAACTACAGCAGAA
1681        ------------+----------+----------+----------+----------+----------+ 1740
            CGAGACTCGAGGTAAGAGGAAGTTCTGGAGGGGTTGAAGGGTCCAACTTGATGTCGTCTT

GCCTTTAGAAAGGGCAGGAGGCCGGCTCTCGAGGTCCTCACCTGAAGTGAGCATGCCAGC
1741        ------------+----------+----------+----------+----------+----------+ 1800
            CGGAAATCTTTCCCGTCCTCCGGCCGAGAGCTCCAGGAGTGGACTTCACTCGTACGGTCG

CACTGCAGGAACGCCCCGGGACAGGAATGCCCATTTGTGCAACGAACCCTGACTCCTTCC
1801        ------------+----------+----------+----------+----------+----------+ 1860
            GTGACGTCCTTGCGGGGCCCTGTCCTTACGGGTAAACACGTTGCTTGGGACTGAGGAAGG

TCACCCTGACTTCTCCCCCTCCCTACCCGCGCGCAGGCCAAGTTGCTGAATCAATGGAGC
1861        ------------+----------+----------+----------+----------+----------+ 1920
            AGTGGGACTGAAGAGGGGGAGGGATGGGCGCGCGTCCGGTTCAACGACTTAGTTACCTCG

CCTCCCCAACCCGGGCGTTCCCCAGCGAGGCTTCCTTCCCATCCTCCTGACCACCGGGGC
1921        ------------+----------+----------+----------+----------+----------+ 1980
            GGAGGGGTTGGGCCCGCAAGGGGTCGCTCCGAAGGAAGGGTAGGAGGACTGGTGGCCCCG

TTTTCGTGAGCTCGTCTCTGATCTCGCGCAAGAGTGACACACAGGTGTTCAAAGACGCTT
1981        ------------+----------+----------+----------+----------+----------+ 2040
            AAAAGCACTCGAGCAGAGACTAGAGCGCGTTCTCACTGTGTGTCCACAAGTTTCTGCGAA

CTGGGGAGTGAGGGAAGCGGTTTACGAGTGACTTGGCTGGAGCCTCAGGGGCGGGCACTG
2041        ------------+----------+----------+----------+----------+----------+ 2100
            GACCCCTCACTCCCTTCGCCAAATGCTCACTGAACCGACCTCGGAGTCCCCGCCCGTGAC

GCACGGAACACACCCTGAGGCCAGCCCTGGCTGCCCAGGCGGAGCTGCCTCTTCTCCCGC
2101        ------------+----------+----------+----------+----------+----------+ 2160
            CGTGCCTTGTGTGGGACTCCGGTCGGGACCGACGGGTCCGCCTCGACGGAGAAGAGGGCG

GGACATGTACAGAGCTCGAGAAGTACTAGTGGCCACGTGGGCCGTGCACCTTAAGCTTTA
2161        ------------+----------+----------+----------+----------+----------+ 2220
            CCTGTACATGTCTCGAGCTCTTCATGATCACCGGTGCACCCGGCACGTGGAATTCGAAAT

<---- 4.p53-BE
                                                               (intron)
            GGGTCGCTGGAGGGGGACCCCGGTTGGAGAGAGGAGCGGAACTCCTGGACAAGCCCTGAC
2221        ------------+----------+----------+----------+----------+----------+ 2280
            CCCAGCGACCTCCCCCTGGGGCCAACCTCTCTCCTCGCCTTGAGGACCTGTTCGGGACTG

----->

AAGCCAAGCCAAAGGTCCGCTCCGGCGCGGGTGGGTGAGTGCGCGCCGCCCCGCGGGGC
2281        ------------+----------+----------+----------+----------+----------+ 2340
            TTCGGTTCGGTTTCCAGGCGAGGCCGCGCCCACCCACTCACGCGCGGCGGGGCGCCCCG

GGGGAGAGAGCCTGCAGCCTTCAGAACAGATATTGCTCATTTTCTGGCAGTTCTCAGACG
2341        ------------+----------+----------+----------+----------+----------+ 2400
            CCCCTCTCTCGGACGTCGGAAGTCTTGTCTATAACGAGTAAAAGACCGTCAAGAGTCTGC
```

Fig. 9C

```
        TAGGAAATAAGTCAGCACCGAAGCAGTGGTTAAGCCGGAGGGCTCGGAAGAACGGCACCT
2401    ------------+---------+---------+---------+---------+---------+ 2460
        ATCCTTTATTCAGTCGTGGCTTCGTCACCAATTCGGCCTCCCGAGCCTTCTTGCCGTGGA

TTTCTTTCTCGAAAAAGTTATATGGGGGCTGAATGAGCTTCTGGAGGCTTGTTTACCGTT
2461    ------------+---------+---------+---------+---------+---------+ 2520
        AAAGAAAGAGCTTTTTCAATATACCCCCGACTTACTCGAAGACCTCCGAACAAATGGCAA

TTTTATTGTCACACAGAAAAGGAAACTGCCTTGTCTCCCTTCCGGGAATTCTCTCTTTAA
2521    ------------+---------+---------+---------+---------+---------+ 2580
        AAAATAACAGTGTGTCTTTTCCTTTGACGGAACAGAGGGAAGGCCCTTAAGAGAGAAATT

GACTGTAAGTCGCTGCCTGAGTGGTTTCATTTTGTTTTGTTTTTCTGCCCTTCTCTTTCT
2581    ------------+---------+---------+---------+---------+---------+ 2640
        CTGACATTCAGCGACGGACTCACCAAAGTAAAACAAAACAAAAAGACGGGAAGAGAAAGA

TCTTTTGCCCTTTCTTAGCTTGCACTCCCATGGTGATTTCTGCTTGGTCTCCTGCTGGGG
2641    ------------+---------+---------+---------+---------+---------+ 2700
        AGAAAACGGGAAAGAATCGAACGTGAGGGTACCACTAAAGACGAACCAGAGGACGACCCC

TTGGTGGTACTCGTTCCCACCGCACAGAACCCGGCGCCTATTATTGGCCAAGAAACTTGA
2701    ------------+---------+---------+---------+---------+---------+ 2760
        AACCACCATGAGCAAGGGTGGCGTGTCTTGGGCCGCGGATAATAACCGGTTCTTTGAACT

GCAGCCTGTTTTGAAAAGTCCCTCGCTCAGAAATGCCAGCTTGCAGATGGCTAATCAAAG
2761    ------------+---------+---------+---------+---------+---------+ 2820
        CGTCGGACAAAACTTTTCAGGGAGCGAGTCTTTACGGTCGAACGTCTACCGATTAGTTTC

AGACGTG
2821    ------- 2827
        TCTGCAC
```

Fig. 9D

<---- 1.p53-B2 ---
(promoter)

```
     TGAGGACTCTCAGGAATATGCTGGTAAAATAAAAATAACCTTTAGAGATGCCCAAACTGT
  1  ------------+---------+---------+---------+---------+---------+  60
     ACTCCTGAGAGTCCTTATACGACCATTTTATTTTATTGGAAATCTCTACGGGTTTGACA
```

--->

```
     TTTCCCCAGAACACCAGCATTCATTAGGTGTTCATTCAATAGATTCTTCAAAGGATTCCA
 61  ------------+---------+---------+---------+---------+---------+  120
     AAAGGGGTCTTGTGGTCGTAAGTAATCCACAAGTAAGTTATCTAAGAAGTTTCCTAAGGT

AAGGCAAAGAAGTTTGGGGAACAGTATATATAATTACCCAACCCTTTGACATTAGCATAC
121  ------------+---------+---------+---------+---------+---------+  180
     TTCCGTTTCTTCAAACCCCTTGTCATATATATTAATGGGTTGGGAAACTGTAATCGTATG

TAAGGGCCCTGAGAAGTTTTGGATTAAGAAAGTTTTCAAATTAAAGTAACCCAGAATTTT
181  ------------+---------+---------+---------+---------+---------+  240
     ATTCCCGGGACTCTTCAAAACCTAATTCTTTCAAAAGTTTAATTTCATTGGGTCTTAAAA

CTAAGATTATTTGACCATGAAACATATGTCTCCCCACAAAGCACATATTCCTATCTCCTT
241  ------------+---------+---------+---------+---------+---------+  300
     GATTCTAATAAACTGGTACTTTGTATACAGAGGGGTGTTTCGTGTATAAGGATAGAGGAA

GAACTTGAGGATAATTAGACGTACGTGGGTAGAGGGTAGGGGAAGGGGGTATGGCATAGA
301  ------------+---------+---------+---------+---------+---------+  360
     CTTGAACTCCTATTAATCTGCATGCACCCATCTCCCATCCCCTTCCCCCATACCGTATCT

AAGAGCAGGACCTTGGGAGCAAGAATATCTAAGTTTAATTCCTGACTCTGCTATTTATTA
361  ------------+---------+---------+---------+---------+---------+  420
     TTCTCGTCCTGGAACCCTCGTTCTTATAGATTCAAATTAAGGACTGAGACGATAAATAAT
```

<---- 2.p53-B2 ---->
(promoter)

```
     ACTAACCATCTTTGCCAATGTTGCTTAAGCTTTTTTGGCTACATTTTTTTATTTGTAAAG
421  ------------+---------+---------+---------+---------+---------+  480
     TGATTGGTAGAAACGGTTACAACGAATTCGAAAAAACCGATGTAAAAAAATAAACATTTC

TAAGTTTAATAATCACTCATCTCACTGGGCTATAATGATAAGTATTAAGTAAGGAAGATC
481  ------------+---------+---------+---------+---------+---------+  540
     ATTCAAATTATTAGTGAGTAGAGTGACCCGATATTACTATTCATAATTCATTCCTTCTAG

CACATATGTGAGTTGCTGGCTTATAATTCACACTCAAGAGATACTGATTTTGTCAATTGT
541  ------------+---------+---------+---------+---------+---------+  600
     GTGTATACACTCAACGACCGAATATTAAGTGTGAGTTCTCTATGACTAAAACAGTTAACA

CCTTTCCCCTTTTTTTCTCTCTTCCCTCCTTCCATTCCTTCTTCCCTTACCTCTCCTTTC
601  ------------+---------+---------+---------+---------+---------+  660
     GGAAAGGGGAAAAAAAGAGAGAAGGGAGGAAGGTAAGGAAGAAGGGAATGGAGAGGAAAG

CTTCCCTCACACCCCTTTTCCTTCCTTCTTTTTACATTTTTTTATTTAAATGAACTTTTC
661  ------------+---------+---------+---------+---------+---------+  720
     GAAGGGAGTGTGGGGAAAAGGAAGGAAGAAAAATGTAAAAAAATAAATTTACTTGAAAAG

ATTTTGGAATAGTTTTAGGATTTCAAAAAATTTGCAGAGATAATACAGAGAATGCCCATA
721  ------------+---------+---------+---------+---------+---------+  780
     TAAAACCTTATCAAAATCCTAAAGTTTTTTAAACGTCTCTATTATGTCTCTTACGGGTAT
```

Fig. 10A

```
     TACCATCCTCCTTATCCCACTTCTTTTTGTGTCTATTAGATGCTCAGAGTGTGTGCACAA
781  ------------+---------+---------+---------+---------+---------+ 840
     ATGGTAGGAGGAATAGGGTGAAGAAAAACACAGATAATCTACGAGTCTCACACACGTGTT

GGCTGGCACGCCCAGGGTCTTCCTCATGGCACTAACAGTCTACTGAAAGGTGGAACAGAG
841  ------------+---------+---------+---------+---------+---------+ 900
     CCGACCGTGCGGGTCCCAGAAGGAGTACCGTGATTGTCAGATGACTTTCCACCTTGTCTC

ACAAGCCTATCAACACCTACAAGACTGGTGGTAAGTGCAGTGACAGATGCAAAACACAGG
901  ------------+---------+---------+---------+---------+---------+ 960
     TGTTCGGATAGTTGTGGATGTTCTGACCACCATTCACGTCACTGTCTACGTTTTGTGTCC

GTGATGGAAAGCCCTCAGGAGGGTAACCTAACCTAGATTTGAGGGCCCAACAGGCTCCAG
961  ------------+---------+---------+---------+---------+---------+ 1020
     CACTACCTTTCGGGAGTCCTCCCATTGGATTGGATCTAAACTCCCGGGTTGTCCGAGGTC

AAGAAAATGTCAACTGAGAGGAAGCCTGAAGGATGAACAGTGGGCTAAGCAAAGGGTTAT
1021 ------------+---------+---------+---------+---------+---------+ 1080
     TTCTTTTACAGTTGACTCTCCTTCGGACTTCCTACTTGTCACCCGATTCGTTTCCCAATA

TAATGTGTTATTAATGGGTTGAATCTAATTGGGAAGGGAGAGAGGTTGCAGAGTGAGGTG
1081 ------------+---------+---------+---------+---------+---------+ 1140
     ATTACACAATAATTACCCAACTTAGATTAACCCTTCCCTCTCTCCAACGTCTCACTCCAC

CAGAGCTTGGTGGACGATGCCAAAGGAATACTGAAACCTTTAGTGTGTCCAGTCTGGAAC
1141 ------------+---------+---------+---------+---------+---------+ 1200
     GTCTCGAACCACCTGCTACGGTTTCCTTATGACTTTGGAAATCACACAGGTCAGACCTTG

TGCATCCAAATTCAGGTTCAGTAATGATGTCATTATCCAAACATACCTTCTGTAAAATTC
1201 ------------+---------+---------+---------+---------+---------+ 1260
     ACGTAGGTTTAAGTCCAAGTCATTACTACAGTAATAGGTTTGTATGGAAGACATTTTAAG

<---- 3.p53-BE ---->
              (promoter)
     ATGCTAAACTACCTAAGAGCTATCTACCGTTCCAAAGCAATAGTGACTTTGAACAGTGTT
1261 ------------+---------+---------+---------+---------+---------+ 1320
     TACGATTTGATGGATTCTCGATAGATGGCAAGGTTTCGTTATCACTGAAACTTGTCACAA CACCAGAGCACGAAAGAATTACAAGATTTTTTTTTAAAGAAAATTGGCCAGGAAATAATG
1321 ------------+---------+---------+---------+---------+---------+ 1380
     GTGGTCTCGTGCTTTCTTAATGTTCTAAAAAAAAAATTTCTTTTAACCGGTCCTTTATTAC AGTAACGAAGGACAGGAAGTAATTGTGAATGTTTAATATAGCTGGGGCTATGCGATTTGG
1381 ------------+---------+---------+---------+---------+---------+ 1440
     TCATTGCTTCCTGTCCTTCATTAACACTTACAAATTATATCGACCCCGATACGCTAAACC CTTAAGTTGTTAGCTTTGTTTTCCTCTTGAGAAATAAAAACTAAGGGGCCCTCCCTTTTC
1441 ------------+---------+---------+---------+---------+---------+ 1500
     GAATTCAACAATCGAAACAAAAGGAGAACTCTTTATTTTTGATTCCCCGGGAGGGAAAAG AGAGCCTTATGGCGCAACATCTGTACTTTTTCATATGGTTAACTGTCCATTCCAGAAACG
1501 ------------+---------+---------+---------+---------+---------+ 1560
     TCTCGGAATACCGCGTTGTAGACATGAAAAAGTATACCAATTGACAGGTAAGGTCTTTGC TCTGTGAGCCTCTCATGTTGCAGCCACAACATGGACAGCCCAGTCAAATGCCCCGCAAGT
1561 ------------+---------+---------+---------+---------+---------+ 1620
     AGACACTCGGAGAGTACAACGTCGGTGTTGTACCTGTCGGGTCAGTTTACGGGGCGTTCA CTTTCTCTGAGTGACTCCAGCAATTAGCCAAGGCTCCTGTACCCAGGCAGGACCTCTGCG
1621 ------------+---------+---------+---------+---------+---------+ 1680
     GAAAGAGACTCACTGAGGTCGTTAATCGGTTCCGAGGACATGGGTCCGTCCTGGAGACGC CTCTGAGCTCCATTCTCCTTCAAGACCTCCCCAACTTCCCAGGTTGAACTACAGCAGAAG
1681 ------------+---------+---------+---------+---------+---------+ 1740
     GAGACTCGAGGTAAGAGGAAGTTCTGGAGGGGTTGAAGGGTCCAACTTGATGTCGTCTTC
```

Fig. 10B

```
       CCTTTAGAAAGGGCAGGAGGCCGGCTCTCGAGGTCCTCACCTGAAGTGAGCATGCCAGCC
1741   ------------+----------+----------+----------+----------+----------+  1800
       GGAAATCTTTCCCGTCCTCCGGCCGAGAGCTCCAGGAGTGGACTTCACTCGTACGGTCGG

ACTGCAGGAACGCCCCGGGACAGGAATGCCCATTTGTGCAACGAACCCTGACTCCTTCCT
1801   ------------+----------+----------+----------+----------+----------+  1860
       TGACGTCCTTGCGGGGCCCTGTCCTTACGGGTAAACACGTTGCTTGGGACTGAGGAAGGA

CACCCTGACTTCTCCCCCTCCCTACCCGCGCGCAGGCCAAGTTGCTGAATCAATGGAGCC
1861   ------------+----------+----------+----------+----------+----------+  1920
       GTGGGACTGAAGAGGGGGAGGGATGGGCGCGCGTCCGGTTCAACGACTTAGTTACCTCGG

CTCCCCAACCCGGGCGTTCCCCAGCGAGGCTTCCTTCCCATCCTCCTGACCACCGGGGCT
1921   ------------+----------+----------+----------+----------+----------+  1980
       GAGGGGTTGGGCCCGCAAGGGGTCGCTCCGAAGGAAGGGTAGGAGGACTGGTGGCCCCGA

TTTCGTGAGCTCGTCTCTGATCTCGCGCAAGAGTGACACACAGGTGTTCAAAGACGCTTC
1981   ------------+----------+----------+----------+----------+----------+  2040
       AAAGCACTCGAGCAGAGACTAGAGCGCGTTCTCACTGTGTGTCCACAAGTTTCTGCGAAG

TGGGGAGTGAGGGAAGCGGTTTACGAGTGACTTGGCTGGAGCCTCAGGGGCGGGCACTGG
2041   ------------+----------+----------+----------+----------+----------+  2100
       ACCCCTCACTCCCTTCGCCAAATGCTCACTGAACCGACCTCGGAGTCCCCGCCCGTGACC

CACGGAACACACCCTGAGGCCAGCCCTGGCTGCCCAGGCGGAGCTGCCTCTTCTCCCGCG
2101   ------------+----------+----------+----------+----------+----------+  2160
       GTGCCTTGTGTGGGACTCCGGTCGGGACCGACGGGTCCGCCTCGACGGAGAAGAGGGCGC

GGTTGGTGGACCCGCTCAGTACGGAGTTGGGGAAGCTCTTTCACTTCGGAGGATTGCTCA
2161   ------------+----------+----------+----------+----------+----------+  2220
       CCAACCACCTGGGCGAGTCATGCCTCAACCCCTTCGAGAAAGTGAAGCCTCCTAACGAGT

ACAACCATGCTGGGCATCTGGACCCTCCTACCTCTGGTGATCCCTCTCCTGCCCGGGTGG
2221   ------------+----------+----------+----------+----------+----------+  2280
       TGTTGGTACGACCCGTAGACCTGGGAGGATGGAGACCACTAGGGAGAGGACGGGCCCACC

AGGCTTACCCCGTCTTAGTCCCGGGGATAGGCAAAGTGGGGCGGGCGCGGGACGCGTGCG
2281   ------------+----------+----------+----------+----------+----------+  2340
       TCCGAATGGGGCAGAATCAGGGCCCCTATCCGTTTCACCCCGCCCGCGCCCTGCGCACGC

GGATTGCGGCGGCAGCGGCGCACGCGGGCACCTGGGAGCGGCGGGCTGCTGCGGGAGGCG
2341   ------------+----------+----------+----------+----------+----------+  2400
       CCTAACGCCGCCGTCGCCGCGTGCGCCCGTGGACCCTCGCCGCCCGACGACGCCCTCCGC

TTGGAGACTGGCTCCCGGGGGCTGTTAGGACCTTCCCTCAGGCCCGGGTGCTCAGAACGA
2401   ------------+----------+----------+----------+----------+----------+  2460
       AACCTCTGACCGAGGGCCCCCGACAATCCTGGAAGGGAGTCCGGGCCCACGAGTCTTGCT

TGGAGGACTTGCTTTTCTTGGGCCTTGATGCGAAGTGCTGATCCCGCTGGGCAGGCGGGG
2461   ------------+----------+----------+----------+----------+----------+  2520
       ACCTCCTGAACGAAAAGAACCCGGAACTACGCTTCACGACTAGGGCGACCCGTCCGCCCC

CAGCTCCGGCGCTCCTCGGAGACCACTGCGCTCCACGTTGAGGTGGGCGTGGGGGCGGA
2521   ------------+----------+----------+----------+----------+----------+  2580
       GTCGAGGCCGCGAGGAGCCTCTGGTGACGCGAGGTGCAACTCCACCCGCACCCCCGCCT

CAGGAATTGAAGCGGAAGTCTGGGAAGCTTTAGGGTCGCTGGAGGGGGACCCCGGTTGGA
2581   ------------+----------+----------+----------+----------+----------+  2640
       GTCCTTAACTTCGCCTTCAGACCCTTCGAAATCCCAGCGACCTCCCCCTGGGGCCAACCT

<---- 4.p53-BE ---->
                      (intron)
       GAGAGGAGCGGAACTCCTGGACAAGCCCTGACAAGCCAAGCCAAAGGTCCGCTCCGGCGC
2641   ------------+----------+----------+----------+----------+----------+  2700
       CTCTCCTCGCCTTGAGGACCTGTTCGGGACTGTTCGGTTCGGTTTCCAGGCGAGGCCGCG
```

Fig. 10C

```
        GGGTGGGTGAGTGCGCGCCGCCCCGCGGGGGCGGGGAGAGAGCCTACAGCCTTCAGAACA
2701    ---------+---------+---------+---------+---------+---------+ 2760
        CCCACCCACTCACGCGCGGCGGGGCGCCCCCGCCCCTCTCTCGGATGTCGGAAGTCTTGT

CATATTGCTCATTTTCTGGCAGTTCTCAGACGTAGGAAATAAGTCAGCACCGAAGCAGTG
2761    ---------+---------+---------+---------+---------+---------+ 2820
        GTATAACGAGTAAAAGACCGTCAAGAGTCTGCATCCTTTATTCAGTCGTGGCTTCGTCAC

GTTAAGCCGGAGGGCTCGGAAGAACGGCACCTTTTCTTTCTCGAAAAAGTTATATGGGGG
2821    ---------+---------+---------+---------+---------+---------+ 2880
        CAATTCGGCCTCCCGAGCCTTCTTGCCGTGGAAAAGAAAGAGCTTTTTCAATATACCCCC

CTGAATGAGCTTCTGGAGGCTTGTTTACCGTTTTTTATTGTCACACAGAAAAGGAAACTG
2881    ---------+---------+---------+---------+---------+---------+ 2940
        GACTTACTCGAAGACCTCCGAACAAATGGCAAAAAATAACAGTGTGTCTTTTCCTTTGAC

CCTTGTCTCCCTTCCGGGAATTCTCTCTTTAAGACTGTAAGTCGCTGCCTGAGTGGTTTC
2941    ---------+---------+---------+---------+---------+---------+ 3000
        GGAACAGAGGGAAGGCCCTTAAGAGAGAAATTCTGACATTCAGCGACGGACTCACCAAAG

ATTTTGTTTTGTTTTTCTGCCCTTCTCTTTCTTCTTTTGCCCTTTCTTAGCTTGCACTCC
3001    ---------+---------+---------+---------+---------+---------+ 3060
        TAAAACAAAACAAAAAGACGGGAAGAGAAAGAAGAAAACGGGAAAGAATCGAACGTGAGG

CATGGTGATTTCTGCTTGGTCTCCTGCTGGGGTTGGTGGTACTCGTTCCCACCGCACAGA
3061    ---------+---------+---------+---------+---------+---------+ 3120
        GTACCACTAAAGACGAACCAGAGGACGACCCCAACCACCATGAGCAAGGGTGGCGTGTCT

ACCCGGCGCCTATTATTGGCCAAGAAACTTGAGCAGCCTGTTTTGAAAAGTCCCTCGCTC
3121    ---------+---------+---------+---------+---------+---------+ 3180
        TGGGCCGCGGATAATAACCGGTTCTTTGAACTCGTCGGACAAAACTTTTCAGGGAGCGAG

AGAAATGCCAGCTTGCAGATGGCTAATCAAAG
3181    ---------+---------+---------+-- 3212
        TCTTTACGGTCGAACGTCTACCGATTAGTTTC
```

Fig. 10D

Fig. 11A variations in the p53 binding region of figure 8

1. p1140 IMI p1140            GGACAAGCCCTGACAAGCCA p1140 IMI        GGAAAGCCCTGACAAGCCA
                    ↑ positions of the mutations (boldface and arrow): 2270 (C→A)

2. p1140 IMII p1140            GGACAAGCCCTGACAAGCCA p1140 IMII       GGAAAGCCCTGAAAGCCA
                    ↑          ↑ positions of the mutations (boldface and arrow): 2270 (C→A)
2280 (C→A)

3. p1140 IMIII p1140            GGACAAGCCCTGACAAGCCA p1140 IMIII      GGAAAT CCCTGAAATCCA
                    ↑ ↑        ↑ ↑ positions of the mutations (boldface and arrow): 2270 (C→A)
2273 (G→T)
2280 (C→A)
2283 (G→T)

Fig. 11B

4. p1140 IMIV p1140         GGACAAGCCCTGACAAGCCA p1140 IMIV    GCACAAGCCCTCACAAGCCA
              ↑          ↑ positions of the mutations (boldface and arrow): 2268 (G→T)

2278 (C→A)

Fig. 12A variations in the p53 binding regions of figure 9

1. p1141 IMIII

| p1141 | GGACAAGCCCTGACAAGCCA |
|---|---|
| p1141 IMIII | GGAAATCCCTGAAATCCA | positions of the mutations (boldface and arrow): 2270
2273
2280
2283

2. p1141 1p53

| p1141 | AGAGATGCCCAAACTGTTTT |
|---|---|
| p1141 1p53 | AGAGATTCCCAAAATGTTTT | positions of the mutations (boldface and arrow): 50
57

3. p1141 2p53

| p1141 | AATGTTGCTTAAGCTTTTTT |
|---|---|
| p1141 2p53 | AATGTTTCTTAAGATTTTTT | positions of the mutations (boldface and arrow): 443
450

Fig. 12B

4. p1141 3p53 p1141          AAACTACCTAAGAGCTATCT p1141 3p53   ACAATACCTAAGAGCTATCT
                    ↑ ↑ positions of the mutations (boldface and arrow): 1268      (A→C)
                                               1270      (C→A)

5. p1141 ΔBgl

<---- 1.p53-BE ---->
p1141         AATAACCTTTAGAGATGCCCAAACTGTTTTCCCCAGAACA
p1141ΔBgl    AATAACCTTTA---------------GATCTCCCCAGAACA

6. p1141 ΔSpe

<---- 2.p53-BE ---->
p1141         CATCTTTGCCAATGTTGCTTAAGCTTTTTTGGCTACATTT
p1141ΔBgl    CATCTTTGCCA--------------CTAGTGGCTACATTT

7. p1141 ΔMph

<---- 3.p53-BE ---->
p1141         AATTCATGCTAAACTACCTAAGAGCTATCTACCGTTCCAA
p1141ΔBgl    AATTCATGCTATGCA---------------TACCGTTCCAA

Fig. 13A variations in the p53 binding region of figure 10

1. p1142 TAG mutation of the positions:   2227  (A→T)

2228  (T→A)

2. p1142 IMIII p1142           GGACAAGCCCTGACAAGCCA p1142 IMIII     GGAAAATCCCTGAAAATCCA
                     ↑  ↑      ↑  ↑ positions of the mutations (boldface and arrow):  2662  (C→A)

2665  (G→T)

2672  (C→A)

2675  (G→T)

3. p1142 ΔBgl

```
                   <---- 1.p53-BE ---->
   p1142       AATAACCTTTAGAGATGCCCAAACTGTTTTCCCCAGAACA
   p1142ΔBgl   AATAACCTTTA--------------GATCTCCCCAGAACA
   ```

4. p1142 ΔSpe

```
                   <---- 2.p53-BE ---->
   p1142       CATCTTTGCCAATGTTGCTTAAGCTTTTTTGGCTACATTT
   p1142ΔBgl   CATCTTTGCCA--------------CTAGTGGCTACATTT
   ```

Fig. 13B 5.  p1142 ΔMph

```
                 <---- 3.p53-BE ---->
p1142       AATTCATGCTAAACTACCTAAGAGCTATCTACCGTTCCAA
p1142ΔBgl   AATTCATGCTATGCA---------------TACCGTTCCAA
```

P53 BINDING AREAS

This application is a continuation and claims priority of International Patent Application No. PCT/DE99/03343 filed Oct. 18, 1999 which in turn claims priority of German Patent Application No. 198 47 779.1 filed on Oct. 16, 1998.

The present invention relates to p53 binding areas (regions) on a CD95 receptor DNA and to the use of the p53 binding regions for influencing apoptosis and/or for identifying substances suitable for this purpose.

p53 is a tumor suppressor which is induced in the case of DNA damage. It then activates target genes so as to achieve growth stand-still in the cells having DNA damage followed by the repair of the DNA damage or death of the cells. The latter is due to apoptosis.

A chemotherapy is to cause DNA damage in tumor cells. This damage shall then lead to the induction of p53 and ultimately to the death of the tumor cells. However, it shows frequently that certain tumor cells are resistant to chemotherapeutic agents or become resistant thereto after a short treatment duration. The reason why this is the case is not really known thus far.

Therefore, it is the object of the present invention to provide a product by which the resistance to chemotherapeutic agents can be investigated and optionally influenced.

According to the invention this is achieved by the subject matters defined in the claims.

The present invention is based on applicant's insights that the induction of p53 by chemotherapeutic agents directly activates apoptosis. In particular, applicant found that p53 activates CD95-mediated apoptosis in that p53 induces both the expression of the CD95 ligand and that of the CD95 receptor. Applicant also found that p53 binds to CD95 receptor DNA via p53 binding regions. He also identified such bindings regions in intron 1 and/or the promoter of the CD95 receptor DNA. Moreover, applicant recognized that resistance to chemotherapeutic agents may be due to the fact that p53 can no longer bind to the above p53 binding regions (cf. Table 1 and FIGS. 1–6).

According to the invention applicant's insight are used to provide a p53 binding region of a CD95 receptor DNA.

The term "p53 binding region" comprises any region of a CD95 receptor DNA to which a p53 may bind and activate the CD95 receptor DNA, i.e. may induce it to transcribe. The term "p53" comprises p53 in wild-type form as well as p53 in modified form which still has the above function. A p53 binding region according to the invention may be identified and provided by common methods. It is favorable to cleave a CD95 receptor DNA (cf. Behrmann, I. et al., Eur. J. Immunol. 24 (1994), 3057–3962) by Sau 3A1 and insert the fragments in the BamHI site of pBlueScript II KS⁺. The cloned CD95 receptor DNA fragments are inserted in DNA binding experiments which use cell extracts from the tumor cells, e.g. H1299, Hep3B, HepG2 or Huh7, which had been transfected beforehand with a p53-coding expression vector, e.g. pCMVp53wt. Bound DNA fragments are fused with a reporter DNA, e.g. luciferase DNA. This may be made e.g. in the expression vectors pGL3-Basic (Promega company) or pTATA-LUC (Wirth, T., Wurzburg, Germany). Resulting expression plasmids are tested in luciferase activity tests for their capacity of being activable.

In a preferred embodiment, a p53 binding region comprises the sequence of FIG. 4, (p53 Be sequence)(SEQ ID NO. 24) and/or FIG. 5 (SEQ ID NOs. 12, 14 and 16)(one or more of the p53 Be sequences) or a sequence differing therefrom by one or more base pairs. The expression "a sequence differing by one or more base pairs" comprises a sequence of a CD95 receptor DNA which hybridizes with the DNA of FIG. 4 (SEQ ID NOs. 24 and 32 ) and/or FIG. 5 (SEQ ID NO. 12, 14 and 16 ) and to which a p53 may bind and which may activate the CD95 receptor DNA. The sequence may differ from the DNA of FIG. 4 and/or FIG. 5 by additions, deletions, substitutions and/or inversions of one or more base pairs. The expression "hybridization" refers to hybridization under common conditions, in particular at 20° C. below the melting point of the sequence.

In a particularly preferred embodiment a p53 binding region comprises the sequence of FIGS. 7, (SEQ ID NO. 2), 8 (SEQ ID NO. 3), 9 (SEQ ID NO. 4), 10 (SEQ ID NO. 1), 11 (SEQ ID NOs. 6, 7, 8, and 9), 12 (SEQ ID NOs. 11, 13, 15, 17 and 19) or 13 (SEQ ID NOs. 25, 27, 29 and 31), the sequences of FIGS. 11, 12 and 13 being variations of the sequences of FIGS. 8, 9, and 10, respectively. Furthermore, the sequences of FIGS. 7, 8, 9 and 10 are explained in FIG. 14.

A p53 binding region according to the invention may be present as such or in combination with any other DNA. For example, a p53 binding region according to the invention may be present in a vector, optionally in combination with a reporter DNA, e.g. luciferase DNA. Preferred combinations are the DNA constructs CD95 (Ps)-LUC, CD95 (P)-LUC, CD95 (I+SV)-LUC, CD95 (Ps+I)-LUC, p1139, p1140, p1141, p1142, p1140 IMI, p1140 IMII, p1140 IMIII, p1140 IMIV, p1141 IMIJI, p1141 1p53 , p1141 2p53 , p1141 3p53 , p1141 ΔBgI, p1141 ΔSpe, p1141 ΔMph, p1142 TAG, p1142 IMIII, p1142 ΔBg1, p1142 ΔSpe and p1142 ΔMph, in which a p53 binding region according to the invention is present in the expression vectors pGL3-Basic and/or pTATA-LUC. As to the DNA constructs CD95 (Ps)-LUC, CD95 (P)-LUC, CD95 (I+SV)-LUC, CD95 (Ps+1)-LUC, reference is made to Example 3 and FIG. 6. The DNA constructs p1139, p1140, p1141, p1142, p1140 IMI, p1140 IMII, p1140 IMIII, p1140 IMIV, p1141 IMIIJ, p1141 1p53 , p1141 2p53 , p1141 3p53, p1141 ΔBgl, p1141 ΔSpe, p1141 ΔMph, p1142 TAG, p1142 IMJI, p1142 ΔBgl, p1142 ΔSpe, and p1142 ΔMph, in which a p53 region according to the invention is present in the expression vectors pGL-3Basic and/or pTATA-LUC. As to the DNA constructs CD95(Ps)-LUC, CD95(P)-LUC, CD95(I+SV)-LUC, CD95(Ps+1)-LUC, reference is made to Example 3 and FIG. 6. The DNA constructs p1139, p1140, p1141, p1142, p1140 IMI, p1140 IMII, p1140 IMIII, p1140 IMIV, p1141 IMIIJ, p1141 1p53, p1141 2p53, p1141 3p53, p1141 ΔBgl, p1141 ΔSpe, p1141 ΔMph, p1142 TAG, p1142 IMJI, p1142 ΔBgl, p1142 ΔSpe, and p1142 ΔMph contain the sequences indicated in FIGS. 7 (SEQ ID NO. 2), 8 (SEQ ID NO. 3), 9 (SEQ ID NO. 4), or 10 (SEQ ID NO. 1), i.e. p53 binding regions or variations thereof (cf. FIG. 11 (SEQ ID NOs. 6, 7, 8 and 9), 12 (SEQ ID NOs. 11, 23, 25 17 and 19) and 13 (SEQ ID NOs. 25, 27, 29, and 31)). The DNA constructs p1139, p1140, p1141 and p1142 are preferred and were deposited with DSMZ (Deutsche Sammiung fur Mikroorganismen und Zellen [German-type collection of microorganisms and cells]) on Sep. 24, 1999, i.e. p1139 under DSM 3075, p1140 under DSM 13062, p1141 under DSN 13063 and p1142 under DSM 13064.

A further subject matter of the present invention is a kit comprising a p53 binding region according to the invention (a) and common auxiliary ingredients (b), such as buffers, solvents, carriers, controls, etc. One or more representatives of the p53 binding region may be present. The above explanations also apply correspondingly.

The present invention enables mechanisms resulting when DNA is damaged to be investigated on a molecular level. Such mechanisms comprise the response of the cells to eliminate the DNA damage or to kill themselves. The latter is an apoptotic process. The present invention enables mechanisms resulting in a chemotherapy to be investigated. In particular, it is possible to investigate the cause of resistances to chemotherapeutic agents. For example, it can be determined by means of a p53 binding region according to the invention whether tumor cell-derived p53 is still capable of inducing apoptosis.

The present invention is also suitable to identify and provide substances capable of influencing apoptosis. This influence may be an induction or an inhibition. For this purpose, it is favorable to introduce into cells a p53 binding region according to the invention in combination with a reporter DNA, add thereto the substances to be identified and select them for the transcription-activating or transcription-inhibiting effect of the substances. p53 binding regions may be activated or inhibited in a CD95 receptor DNA by means of these substances and therefore induce or inhibit apoptosis.

Thus, the present invention provides products or means serving for influencing apoptotic processes. This is of great significance, since apoptotic processes are modified in many diseases. For example, the apoptosis rate of viral, liver and neurodegenerative diseases is increased whereas it is lowered in autoimmune and tumoral diseases. Thus, the present invention is the possibility of therapeutically influencing these diseases. An application in a diagnostic respect is also useful, in particular if a p53 gene therapy is carried out in connection with the above-mentioned diseases and the vectors used for this purpose are tested for effectiveness, availability, etc., by means of the vectors according to the invention.

BRIEF DESCRIPTION OF THE DRAWINGS

FIG. 7 shows the sequence of a p53 binding region according to the invention (SEQ ID NO. 2), the sequence comprising the nucleotides 1–720 of intron I of the CD95 receptor DNA. The p53-BE sequence is marked in boldface.

FIG. 8 shows the sequence of a p53 binding region according to the invention (SEQ ID NO. 3), the sequence comprising nucleotides 448–2154 of the promoter, exon I and the nucleotides 2223–2827 (correspond to nucleotides 116–720 of the sequence of FIG. 7) of intron I of the CD95 receptor DNA. The p53-BE sequences are marked in boldface.

FIG. 9 shows the sequence of a p53 binding region according to the invention (SEQ ID NO. 4), the sequence comprising nucleotides 1–2154 of the promoter, exon I and nucleotides 2223–2827 of intron I of the CD95 receptor DNA. The p53-BE sequences are marked in boldface.

FIG. 10 shows the sequence of a p53 binding region according to the invention (SEQ ID NO. 1), the sequence comprising nucleotides 1–2154 of the promoter, exon I together with its 3' region and nucleotides 2223–2820 of intron I together with its 5'-region of the CD95 receptor DNA. The p53-BE sequences are marked in boldface.

FIG. 11 shows variations in the p53 binding region of FIG. 8 (SEQ ID NOs. 6, 7, 8, and 9), the variations being point mutations in intron I of the CD95 receptor DNA.

FIG. 12 shows variations in the p53 binding region of FIG. 9 (SEQ ID NOs. 11, 13, 15, 17 and 19), the variations being point mutations in intron I and in the promoter as well as deletions in the promoter of the CD95 receptor DNA.

FIG. 13 shows variations in the p53 binding region of FIG. 10 (SEQ ID NOs. 25, 27, 29 and 31), the variations being point mutations in intron I and in exon I as well as deletions in the promoter of the CD95 receptor DNA.

The present invention is explained by the below examples.

EXAMPLE 1

Detection of the Expression of the CD95 Receptor in Tumor Cells Treated with Chemotherapeutic Agents (A) and of the Response of these Tumor Cells to the Induction of Apoptosis by CD95 Receptor Stimulation (B).

Figure 1:
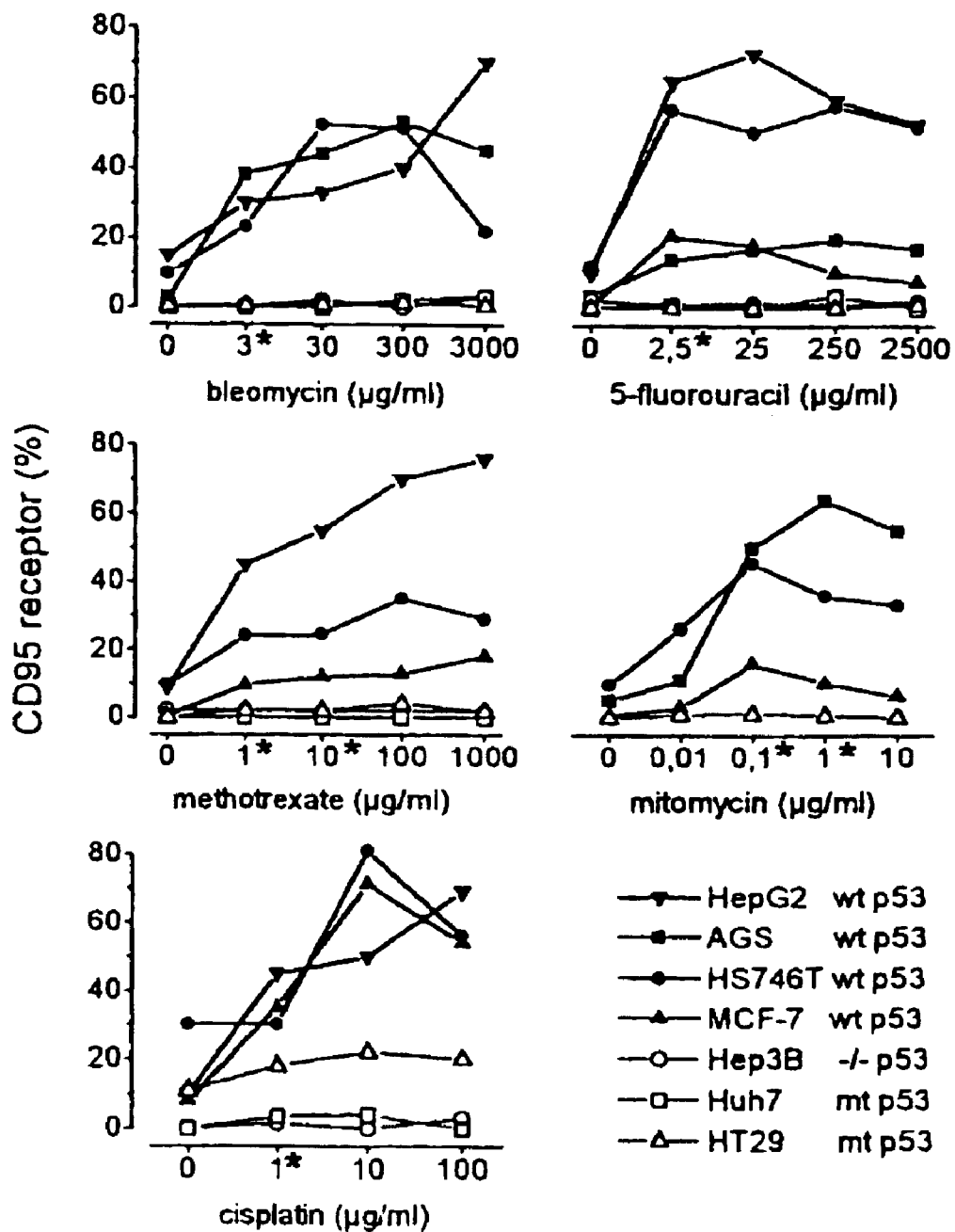
FIG. 1 shows the expression of the CD95 receptor in tumor cells after treating them with chemotherapeutic agents. Clinically relevant concentrations of the chemotherapeutic gents are marked with an asterisk. The tumor cells express p53, no p53 (−/−p53) or p53 disturbed as regards the binding to an inventive p53 binding region of a CD95 receptor DNA (mt p53).

(A) The tumor cells HepG2 (human hepatoblastoma), AGS (colon carcinoma) HS746T (gastric carcinoma), MCF-7 (breast cancer), Hep3B (human hepatoblastoma), Huh7 (hepatocellular carcinoma), and HT29 (colon carcinoma) are treated with the chemotherapeutic agents bleomycin, 5-fluorouracil, methotrexate, mitomycin and cisplatin. HepG2, AGS, HS746T and MC-7 express a p53 which binds to a p53 binding region according to the invention. Hep3B expresses no p53. Huh7 and HT29 express a p53 which is disturbed as regards its binding to a p53 binding region according to the invention. The expression of the CD95 receptor is determined by FACScan. To this end, a biotinylated anti-APO-1 (CD95 receptor) antibody and quantum red-streptavidine (Sigma company) are used as a second reagent for an indirect immunofluorescence (cf. FIG. 1).

It shows that only the tumor cells HepG2, AGS, HS746T and MCF-7 whose p53 binds to a p53 binding region according to the invention, have CD95 receptor expression.

Figure 2:
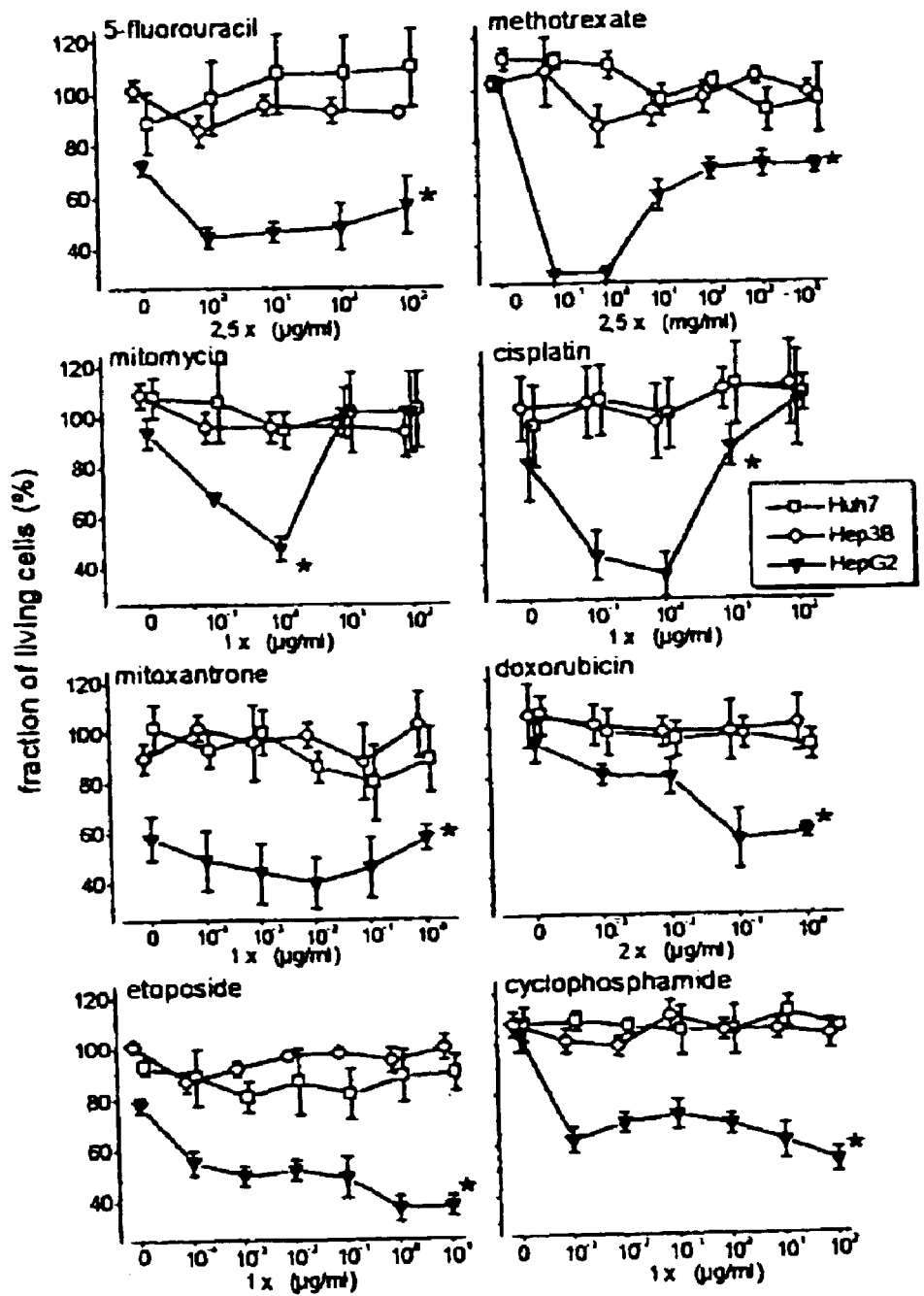
FIG. 2 shows the response of tumor cells treated with chemotherapeutic agents to the induction of apoptosis by CD95 receptor stimulation.

(B) The tumor cells HepG2, Huh7 and Hep3B (cf. (A)) are treated with the chemotherapeutic agents 5-fluorouracil, methotrexate, mitomycin, cisplatin, mitoxantrone, doxorubicin, etoposide and cyclophosphamide for 48 h or another 24 h in combination with 100 ng/ml IgG3 anti-APO-1 antibodies. The antibody effects CD95 receptor stimulation. The living cell fraction is determined. For this purpose, the MTT test is carried out determining the ability of living cells to reduce soluble yellow tetrazolium salt (MTT) to form blue formazan crystals (cf. FIG. 2).

It shows that only the tumor cell HepG2 whose p53 binds to a p53 binding region according to the invention responds more intensely to apoptosis induction.

EXAMPLE 2

Detection of the Expression of the CD95 Receptor in Bleomycin-Treated Tumor Cells, the Tumor Cells Expressing p53 Only Following Transfection.

The tumor cells Hep3B ($0.6 \times 10^6$ cells) which usually express no p53, are transfected with 1 µg of the expression vector pCMVp53wt coding for p53 by means of the calcium phosphate coprecipitation method. Thereafter, the tumor cells are treated with bleomycin.

Figure 3:
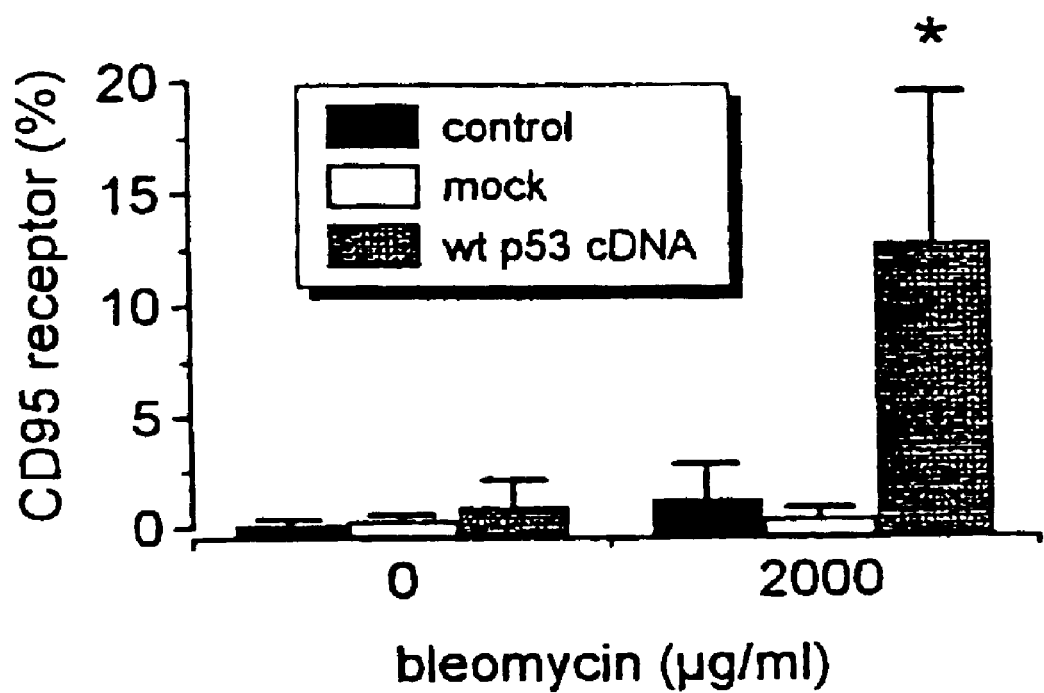
FIG. 3 shows the expression of the CD95 receptor in tumor cells treated with a chemotherapeutic agent, the tumor cells expressing p53 only after transfection with an expression plasmid coding for p53.

The expression of the CD95 receptor is determined by FACScan (cf. Example 1(A); FIG. 3).

It shows that an expression of the CD53 receptor is obtained by the expression of p53.

EXAMPLE 3

Detection of the Expression of Luciferase DNA by p53 Binding to a p53 Binding Region According to the Invention.

Expression plasmids are produced, the expression vector pGL3-Basic being used as the vector. The following CD95 receptor DNA/luciferase-DNA constructs are inserted in this vector:

CD95 (Ps)-LUC

Figure 5:
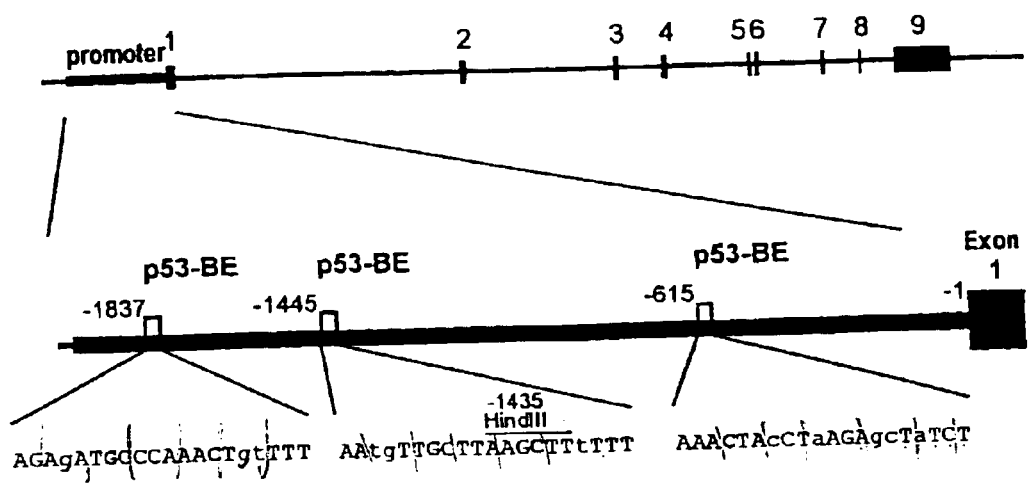
FIG. 5 shows a p53 binding region according to the invention (p53 BE) within the promoter of a CD95 receptor DNA comprising 9 exons. The promoter has three p53 binding regions.

The luciferase-DNA is linked via its 5' end with a 1.43 kb promoter region and the 5' end of exon 1 of the CD95 receptor DNA (HindIII-SacII fragment, cf. FIGS. 5 (SEQ ID NOs. 12, 14 and 16) and 6).

CD95(P)-LUC

The luciferase DNA is linked via its 5' end with a 1.9kb promoter region and the 5' end of exon 1 of CD95 receptor DNA (cf. FIGS. 5 (SEQ ID NOs. 12, 14 and 16) and 6).

CD95(I+SV)-LUC

Figure 4:
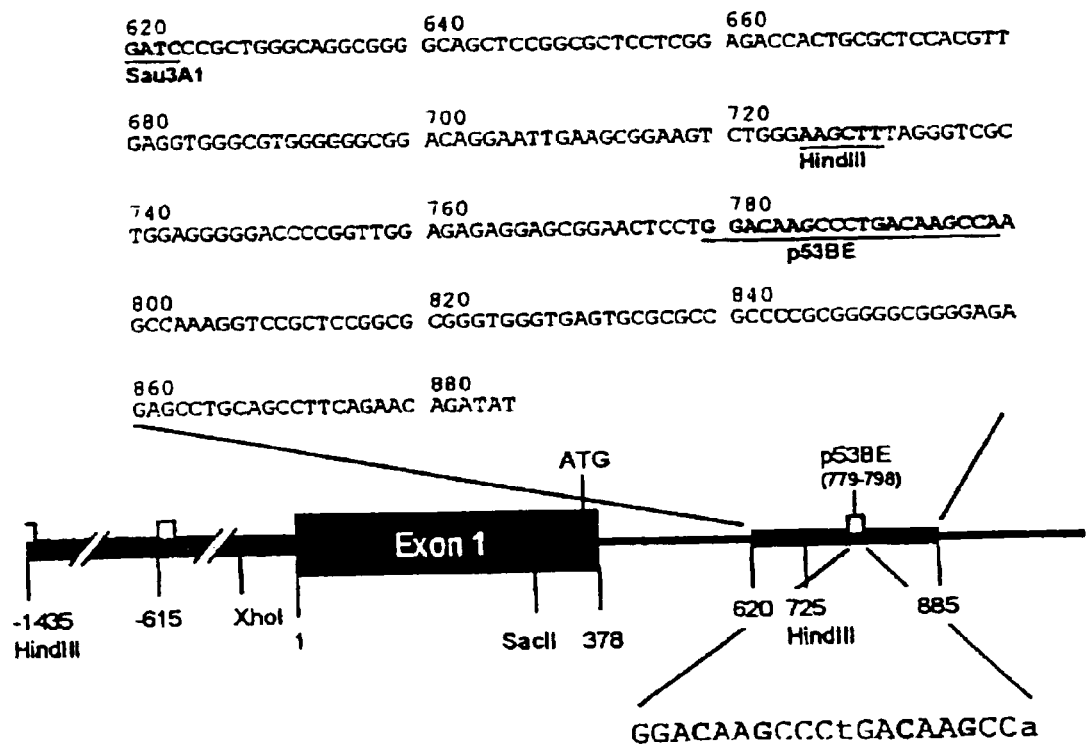
FIG. 4 shows a p53 binding region according to the invention (p53 BE) within intron 1 of a CD95 receptor DNA.

The luciferase DNA is linked via its 5' end with the "minimum" SV40 promoter and a 0.7 kb intron 1 fragment of the CD95 receptor DNA (cf. FIGS. 4 (SEQ ID NOs. 24 and 32) and 6).

The luciferase DNA is linked via its 5' end with a 0.7 kb intron 1 fragment and a 1.43 kb promoter region of the CD95 receptor DNA (cf. FIGS. 4 (SEQ ID NOs. 24 and 32) and 6).

Figure 6:
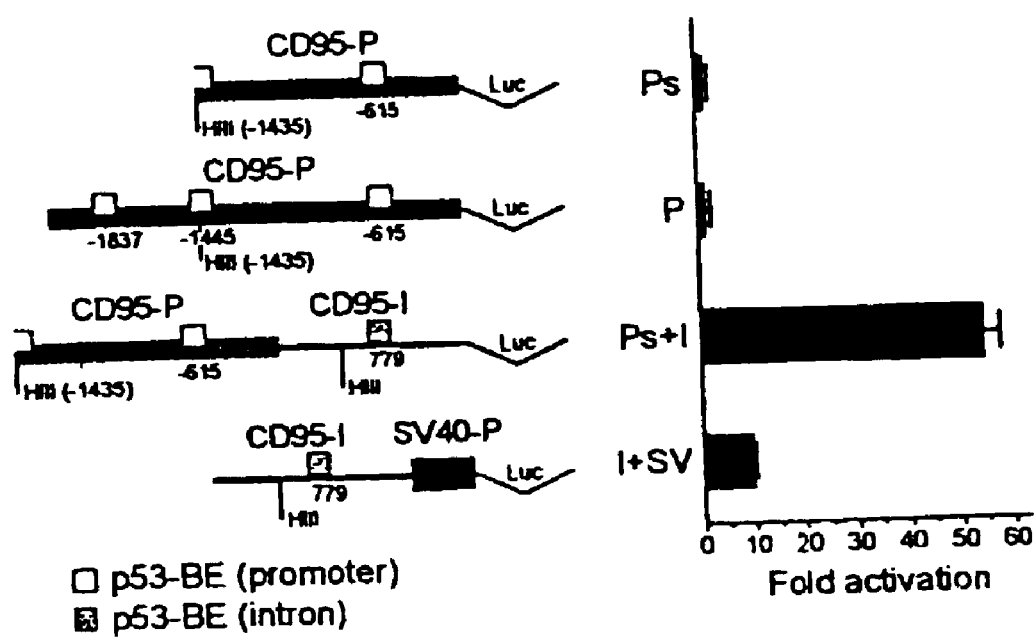
FIG. 6 shows the expression of a luciferase DNA after the binding of p53 to a p53 binding region according to the invention within an expression plasmid containing the luciferase DNA.
Figure 14:
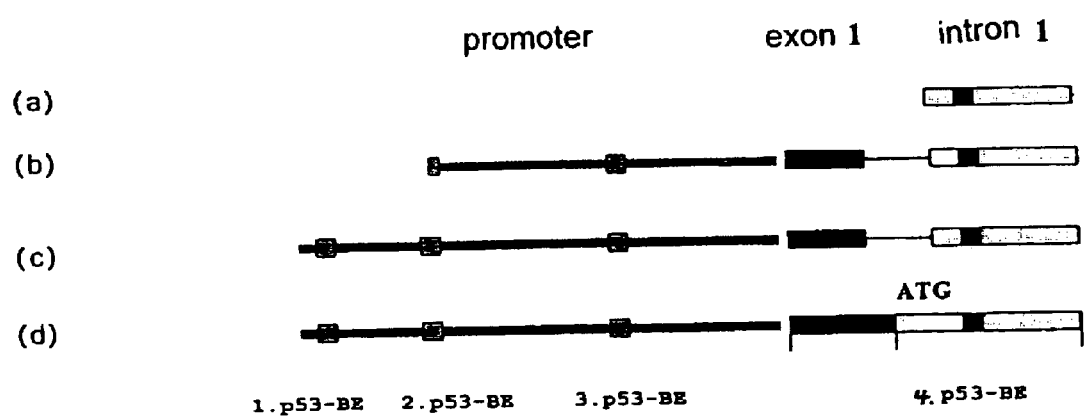
FIG. 14 shows a physical map of p53 binding regions according to the invention, (a) being the binding region of FIG. 7 (SEQ ID NO. 2), (b) being that of FIG. 8 (SEQ ID NO. 3), (c) being that of FIG. 9 (SEQ ID NO. 4), and (d) being that of FIG. 10 (SEQ ID NO. 1).

The above expression plasmids (1 µg each) are transfected in Hep3B tumor cells. The expression vector pCMVp53wt (100 ng each) is also transfected. Both transfections are effected by the calcium phosphate coprecipitation method. A common luciferase test is carried out (cf. FIG. 6).

It shows that the DNA constructs CD95 (PS)-LUC and CD95 (P)-LUC serve for achieving an activation of luciferase which is about 2 times to that of a control. An even more intense activation is obtained when the DNA construct CD95 (I+SV)-LUC and in particular the DNA construct CD95 (PS+I)-LUC are used. In the latter case, the activation has a factor of about 50.

TABLE 1

Induction of p63, the CD95 receptor and of apoptosis by chemotherapeutic agent

| Chemotherapeutic agent | Mode of action | | P53 induction | Induction of apoptosis | CD95 receptor induction | Increased response to induction of apoptosis by CD95 receptor stimulation |
|---|---|---|---|---|---|---|
| Fluorouracil | Antimetabolite | Pyrimidine antagonist | + | + | + | +* |
| Methotrexate | Antimetabolite | Folic acid antagonist | + | + | + | +* |
| Mitomycin | Alkylation | | + | + | + | +* |
| Cisplatin | Alkylation | | + | + | + | +* |
| Cyclophosphamide | Alkylation | | + | + | + | +* |
| Mitoxantron | Intercalation | | + | + | + | +* |
| Doxorubicin | Intercalation | | + | + | + | +* |
| Etoposide | Mitotic blocking | Inhibition of topoisomerase II | + | + | + | +* |
| Bleomycin | Inhibition of DNA polymerase | | + | + | + | +* |

*test for synergism between CD95 receptor stimulation by anti-APO-1 and simultaneous chemotherapeutic treatment: $p < 0.0001$

What is claimed is:

1. An isolated p53 binding region of a human CD95 receptor DNA, wherein p53 may activate the CD95 receptor DNA by binding to the p53 binding region, the isolated p53 binding region comprising SEQ ID NO. 2, SEQ ID NO. 3, SEQ ID NO. 4, SEQ ID NO. 1, SEQ ID NO. 6, SEQ ID NO. 7, SEQ ID NO. 8, SEQ ID NO. 9, SEQ ID NO. 11, SEQ ID NO. 13, SEQ ID NO. 15, SEQ ID NO. 17, SEQ ID NO. 19, SEQ ID NO. 25, SEQ ID NO. 27, SEQ ID NO. 29, SEQ ID NO. 31, SEQ ID NO. 24 or SEQ ID NO. 32.

2. An isolated p53 binding region of a human CD95 receptor DNA, wherein p53 may activate the CD95 receptor DNA by binding to the p53 binding region, the isolated p53 binding region consisting of SEQ ID NO. 10, SEQ ID NO. 12, or SEQ ID NO. 14.

3. A vector comprising at least one of the p53 binding region according to claim 1.

4. The vector according to claim 3, wherein the vector is selected from the group consisting of CD95(Ps)-LUC, CD95 (P)-LUC, CD95 (I+SV)-LUC, CD95(Ps+I)-LUC, p1139, p1140, p1141, p1142, p1140 IMI, p1140 IMII, p1140 IMIII, p1140 IMIV, p1141 IMIII, p1141 1p53, p1141 2p53, p1141 3p53, p1141 ΔBgl, p1141 ΔSpe, p1141 ΔMph, p1142 TAG, p1142 IMIII, p1142 ΔBgl, p1142 ΔSpe, and p1142 ΔMph.

5. A vector comprising at least one isolated p53 binding region of a CD95 receptor DNA, wherein p53 may activate the CD95 receptor DNA by binding to the p53 binding region, and wherein the isolated p53 binding region consists of SEQ ID NO. 10, SEQ ID NO. 12, or SEQ ID NO. 14.

6. The vector according to claim 5, wherein the vector is selected from the group consisting of CD95(Ps)-LUC, CD95(P)-LUC, CD95 (I+SV)-LUC, CD95(Ps+I)-LUC, p1139, p1140, p1141, p1142, p1140 IMI, p1140 IMII, p1140 IMIII, p114 IMIV, p114 IMIII, p1141 1p53, p1141 2p53, p1141 3p53, p1141 ΔBgl, p1141 ΔSpe, p1141 ΔMph, p1142 TAG, p1142 IMIII, p1142 ΔBgl, p1142 ΔSpe, and p1 142 ΔMph.

* * * * *

SEQUENCE LISTING

<160> NUMBER OF SEQ ID NOS: 32

<210> SEQ ID NO 1
<211> LENGTH: 3212
<212> TYPE: DNA
<213> ORGANISM: Homo Sapiens

<400> SEQUENCE: 1

-continued

| | |
|---|---|
| tgaggactct caggaatatg ctggtaaaat aaaaataacc tttagagatg cccaaactgt | 60 |
| tttccccaga acaccagcat tcattaggtg ttcattcaat agattcttca aaggattcca | 120 |
| aaggcaaaga agtttgggga acagtatata taattaccca acctttgac attagcatac | 180 |
| taagggccct gagaagtttt ggattaagaa agttttcaaa ttaaagtaac ccagaatttt | 240 |
| ctaagattat ttgaccatga aacatatgtc tccccacaaa gcacatattc ctatctcctt | 300 |
| gaacttgagg ataattagac gtacgtgggt agagggtagg ggaaggggt atggcataga | 360 |
| aagagcagga ccttgggagc aagaatatct aagtttaatt cctgactctg ctatttatta | 420 |
| actaaccatc tttgccaatg ttgcttaagc tttttttggct acattttttt atttgtaaag | 480 |
| taagtttaat aatcactcat ctcactgggc tataatgata agtattaagt aaggaagatc | 540 |
| cacatatgtg agttgctggc ttataattca cactcaagag atactgattt tgtcaattgt | 600 |
| cctttcccct ttttttctct cttccctcct tccattcctt cttcccttac ctctccttttc | 660 |
| cttccctcac accccttttc cttccttctt tttacatttt tttatttaaa tgaacttttc | 720 |
| attttggaat agttttagga tttcaaaaaa tttgcagaga taatacagag aatgcccata | 780 |
| taccatcctc cttatcccac ttctttttgt gtctattaga tgctcagagt gtgtgcacaa | 840 |
| ggctggcacg cccagggtct tcctcatggc actaacagtc tactgaaagg tggaacagag | 900 |
| acaagcctat caaacctac aagactggtg gtaagtgcag tgacagatgc aaaacacagg | 960 |
| gtgatggaaa gccctcagga gggtaaccta acctagattt gagggcccaa caggctccag | 1020 |
| aagaaaatgt caactgagag gaagcctgaa ggatgaacag tgggctaagc aaagggttat | 1080 |
| taatgtgtta ttaatgggtt gaatctaatt gggaagggag agaggttgca gagtgaggtg | 1140 |
| cagagcttgg tggacgatgc caaaggaata ctgaaacctt tagtgtgtcc agtctggaac | 1200 |
| tgcatccaaa ttcaggttca gtaatgatgt cattatccaa acataccttc tgtaaaattc | 1260 |
| atgctaaact acctaagagc tatctaccgt tccaaagcaa tagtgacttt gaacagtgtt | 1320 |
| caccagagca cgaaagaatt acaagatttt ttttttaaaga aaattggcca ggaaataatg | 1380 |
| agtaacgaag gacaggaagt aattgtgaat gtttaatata gctggggcta tgcgatttgg | 1440 |
| cttaagttgt tagctttgtt ttcctcttga gaaataaaaa ctaagggggcc ctccctttttc | 1500 |
| agagccttat ggcgcaacat ctgtactttt tcatatggtt aactgtccat tccagaaacg | 1560 |
| tctgtgagcc tctcatgttg cagccacaac atggacagcc cagtcaaatg ccccgcaagt | 1620 |
| ctttctctga gtgactccag caattagcca aggctcctgt acccaggcag gacctctgcg | 1680 |
| ctctgagctc cattctcctt caagacctcc ccaacttccc aggttgaact acagcagaag | 1740 |
| cctttagaaa gggcaggagg ccggctctcg aggtcctcac ctgaagtgag catgccagcc | 1800 |
| actgcaggaa cgcccggga caggaatgcc catttgtgca acgaaccctg actccttcct | 1860 |
| caccctgact tctccccctc cctacccgcg cgcaggccaa gttgctgaat caatggagcc | 1920 |
| ctccccaacc cgggcgttcc ccagcgaggc ttccttccca tcctcctgac caccggggct | 1980 |
| tttcgtgagc tcgtctctga tctcgcgcaa gagtgacaca caggtgttca aagacgcttc | 2040 |
| tggggagtga gggaagcggt ttacgagtga cttggctgga gcctcagggg cgggcactgg | 2100 |
| cacggaacac accctgaggc cagccctggc tgcccaggcg agctgcctc ttctcccgcg | 2160 |
| ggttggtgga cccgctcagt acggagttgg ggaagctctt tcacttcgga ggattgctca | 2220 |
| acaaccatgc tgggcatctg acccctccta cctctggtga tccctctcct gcccgggtgg | 2280 |
| aggcttaccc cgtcttagtc ccggggatag gcaaagtggg gcgggcgcgg gacgcgtgcg | 2340 |
| ggattgcggc ggcagcggcg cacgcgggca cctgggagcg gcgggctgct gcgggaggcg | 2400 |

-continued

```
ttggagactg gctcccgggg gctgttagga ccttccctca ggcccgggtg ctcagaacga    2460
tggaggactt gcttttcttg ggccttgatg cgaagtgctg atcccgctgg gcaggcgggg    2520
cagctccggc gctcctcgga gaccactgcg ctccacgttg aggtgggcgt gggggggcgga   2580 caggaattga agcggaagtc tgggaagctt tagggtcgct ggaggggggac cccggttgga   2640 gagaggagcg gaactcctgg acaagccctg acaagccaag ccaaaggtcc gctccggcgc    2700
gggtgggtga gtgcgcgccg ccccgcgggg gcggggagag agcctacagc cttcagaaca    2760
catattgctc attttctggc agttctcaga cgtaggaaat aagtcagcac cgaagcagtg    2820
gttaagccgg agggctcgga agaacggcac cttttctttc tcgaaaaagt tatatggggg    2880
ctgaatgagc ttctggaggc ttgtttaccg ttttttattg tcacacagaa aaggaaactg    2940
ccttgtctcc cttccgggaa ttctctcttt aagactgtaa gtcgctgcct gagtggtttc    3000
attttgtttt gttttttctgc ccttctcttt cttcttttgc cctttcttag cttgcactcc    3060
catggtgatt tctgcttggt ctcctgctgg ggttggtggt actcgttccc accgcacaga    3120
acccggcgcc tattattggc caagaaactt gagcagcctg ttttgaaaag tccctcgctc    3180
agaaatgcca gcttgcagat ggctaatcaa ag                                  3212

<210> SEQ ID NO 2
<211> LENGTH: 720
<212> TYPE: DNA
<213> ORGANISM: Homo Sapiens

<400> SEQUENCE: 2
gatcccgctg ggcaggcggg gcagctccgg cgctcctcgg agaccactgc gctccacgtt     60
gaggtgggcg tgggggggcgg acaggaattg aagcggaagt ctgggaagct ttagggtcgc    120 tggagggggga ccccggttgg agagaggagc ggaactcctg acaagccct gacaagccaa    180 gccaaaggtc cgctccggcg cgggtgggtg agtgcgcgcc gccccgcggg ggcggggaga    240
gagcctacag ccttcagaac acatattgct cattttctgg cagttctcag acgtaggaaa    300
taagtcagca ccgaagcagt ggttaagccg gagggctcgg aagaacggca ccttttcttt    360
ctcgaaaaag ttatatgggg gctgaatgag cttctggagg cttgtttacc gttttttatt    420
gtcacacaga aaaggaaact gccttgtctc cttccggga attctctctt taagactgta     480
agtcgctgcc tgagtggttt cattttgttt tgttttttctg cccttctctt tcttcttttg    540
ccctttctta gcttgcactc ccatggtgat tctgcttgg tctcctgctg gggttggtgg    600
tactcgttcc caccgcacag aacccggcgc ctattattgg ccaagaaact tgagcagcct    660
gttttgaaaa gtccctcgct cagaaatgcc agcttgcaga tggctaatca aagagacgtg    720

<210> SEQ ID NO 3
<211> LENGTH: 2380
<212> TYPE: DNA
<213> ORGANISM: Homo Sapiens

<400> SEQUENCE: 3
agcttttttg gctacatttt tttatttgta aagtaagttt aataatcact catctcactg     60
ggctataatg ataagtatta agtaaggaag atccacatat gtgagttgct ggcttataat    120
tcacactcaa gagatactga ttttgtcaat tgtccttttcc cctttttttc tctcttccct   180
ccttccattc cttcttccct tacctctcct ttccttccct cacacccctt ttccttcctt    240 cttttttacat ttttttatt aaatgaactt ttcattttgg aatagtttta ggatttcaaa    300
```

-continued

| | |
|---|---|
| aaatttgcag agataataca gagaatgccc atataccatc ctccttatcc cacttctttt | 360 |
| tgtgtctatt agatgctcag agtgtgtgca caaggctggc acgcccaggg tcttcctcat | 420 |
| ggcactaaca gtctactgaa aggtggaaca gagacaagcc tatcaacacc tacaagactg | 480 |
| gtggtaagtg cagtgacaga tgcaaaacac agggtgatgg aaagccctca ggagggtaac | 540 |
| ctaacctaga tttgagggcc caaacaggct ccagaagaaa atgtcaactg agaggaagcc | 600 |
| tgaaggatga acagtgggct aagcaaaggg ttattaatgt gttattaatg ggttgaatct | 660 |
| aattgggaag ggagagaggt tgcagagtga ggtgcagagc ttggtggacg atgccaaagg | 720 |
| aatactgaaa cctttagtgt gtccagtctg aactgcatc caaattcagg ttcagtaatg | 780 |
| atgtcattat ccaaacatac cttctgtaaa attcatgcta aactacctaa gagctatcta | 840 |
| ccgttccaaa gcaatagtga ctttgaacag tgttcaccag agcacgaaag aattacaaga | 900 |
| ttttttttta agaaaattg gccaggaaat aatgagtaac aaggacagg aagtaattgt | 960 |
| gaatgtttaa tatagctggg gctatgcgat ttggcttaag ttgttagctt tgttttcctc | 1020 |
| ttgagaaata aaaactaagg ggccctccct tttcagagcc ctatggcgca acatctgtac | 1080 |
| tttttcatat ggttaactgt ccattccagg aacgtctgtg agcctctcat gttgcagcca | 1140 |
| caacatggac agcccagtca aatgccccgc aagtctttct ctgagtgact ccagcaatta | 1200 |
| gccaaggctc ctgtacccag gcaggacctc tgcgctctga gctccattct ccttcaagac | 1260 |
| ctccccaact tcccaggttg aactacagca gaagccttta gaaagggcag gaggccggct | 1320 |
| ctcgaggtcc tcacctgaag tgagcatgcc agccactgca ggaacgcccc gggacaggaa | 1380 |
| tgcccatttg tgcaacgaac cctgactcct tcctcaccct gacttctccc cctccctacc | 1440 |
| cgcgcgcagg ccaagttgct gaatcaatgg agccctcccc aacccgggcg ttccccagcg | 1500 |
| aggcttcctt cccatcctcc tgaccaccgg ggcttttcgt gagctcgtct ctgatctcgc | 1560 |
| gcaagagtga cacacaggtg ttcaaagacg cttctgggga gtgagggaag cggtttacga | 1620 |
| gtgacttggc tggagcctca ggggcgggca ctggcacgga acacaccctg aggccagccc | 1680 |
| tggctgccca ggcggagctg cctcttctcc cgcggacatg tacagagctc gagaagtact | 1740 |
| agtggccacg tgggccgtgc accttaagct ttagggtcgc tggaggggga ccccggttgg | 1800 |
| agagaggagc ggaactcctg acaagcccct gacaagccaa gccaaaggtc cgctccggcg | 1860 |
| cgggtgggtg agtgcgcgcc gccccgcggg ggcggggaga gagcctgcag ccttcagaac | 1920 |
| agatattgct cattttctgg cagttctcag acgtaggaaa taagtcagca ccgaagcagt | 1980 |
| ggttaagccg gagggctcgg aagaacggca ccttttcttt ctcgaaaaag ttatatgggg | 2040 |
| gctgaatgag cttctggagg cttgtttacc gtttttatt gtcacacaga aaaggaaact | 2100 |
| gccttgtctc ccttccggga attctctctt taagactgta agtcgctgcc tgagtggttt | 2160 |
| cattttgttt tgtttttctg cccttctctt tcttcttttg cccttcctta gcttgcactc | 2220 |
| ccatggtgat ttctgcttgg tctcctgctg gggttggtgg tactcgttcc caccgcacag | 2280 |
| aacccggcgc ctattattgg ccaagaaact tgagcagcct gttttgaaaa gtccctcgct | 2340 |
| cagaaatgcc agcttgcaga tggctaatca aagagacgtg | 2380 |

<210> SEQ ID NO 4
<211> LENGTH: 2827
<212> TYPE: DNA
<213> ORGANISM: Homo Sapiens

<400> SEQUENCE: 4

| | |
|---|---|
| tgaggactct caggaatatg ctggtaaaat aaaaataacc tttagagatg cccaaactgt | 60 |

-continued

| | |
|---|---|
| tttccccaga acaccagcat tcattaggtg ttcattcaat agattcttca aaggattcca | 120 |
| aaggcaaaga agtttgggga acagtatata taattaccca acccttttgac attagcatac | 180 |
| taagggccct gagaagtttt ggattaagaa agttttcaaa ttaaagtaac ccagaattt | 240 |
| ctaagattat ttgaccatga acatatgtc tccccacaaa gcacatattc ctatctcctt | 300 |
| gaacttgagg ataattagac gtacgtgggt agagggtagg ggaagggggt atggcataga | 360 |
| aagagcagga ccttgggagc aagaatatct aagtttaatt cctgactctg ctatttatta | 420 |
| actaaccatc tttgccaatg ttgcttaagc ttttttggct acatttttt atttgtaaag | 480 |
| taagtttaat aatcactcat ctcactgggc tataatgata agtattaagt aaggaagatc | 540 |
| cacatatgtg agttgctggc ttataattca cactcaagag atactgattt tgtcaattgt | 600 |
| cctttccct tttttctct cttccctcct tccattcctt cttcccttac ctctcctttc | 660 |
| cttccctcac accccttttc cttccttctt tttacatttt tttatttaaa tgaacttttc | 720 |
| attttggaat agttttagga tttcaaaaaa tttgcagaga taatacagag aatgcccata | 780 |
| taccatcctc cttatcccac ttctttttgt gtctattaga tgctcagagt gtgtgcacaa | 840 |
| ggctggcacg cccagggtct tcctcatggc actaacagtc tactgaaagg tggaacagag | 900 |
| acaagcctat caacacctac aagactggtg gtaagtgcag tgacagatgc aaaacacagg | 960 |
| gtgatggaaa gccctcagga gggtaaccta acctagattt gagggcccaa acaggctcca | 1020 |
| gaagaaaatg tcaactgaga ggaagcctga aggatgaaca gtgggctaag caaagggtta | 1080 |
| ttaatgtgtt attaatgggt tgaatctaat tgggaaggga gagaggttgc agagtgaggt | 1140 |
| gcagagcttg gtggacgatg ccaaaggaat actgaaacct ttagtgtgtc cagtctggaa | 1200 |
| ctgcatccaa attcaggttc agtaatgatg tcattatcca aacataccct ctgtaaaatt | 1260 |
| catgctaaac tacctaagag ctatctaccg ttccaaagca atagtgactt tgaacagtgt | 1320 |
| tcaccagagc acgaaagaat tacaagattt tttttaaag aaaattggcc aggaaataat | 1380 |
| gagtaacgaa ggacaggaag taattgtgaa tgtttaatat agctggggct atgcgatttg | 1440 |
| gcttaagttg ttagctttgt tttcctcttg agaaataaaa actaagggc cctcccttt | 1500 |
| cagagcccta tggcgcaaca tctgtacttt tcatatggt taactgtcca ttccaggaac | 1560 |
| gtctgtgagc ctctcatgtt gcagccacaa catggacagc ccagtcaaat gccccgcaag | 1620 |
| tctttctctg agtgactcca gcaattagcc aaggctcctg tacccaggca ggacctctgc | 1680 |
| gctctgagct ccattctcct tcaagacctc cccaacttcc caggttgaac tacagcagaa | 1740 |
| gcctttagaa agggcaggag gccggctctc gaggtcctca cctgaagtga gcatgccagc | 1800 |
| cactgcagga acgccccggg acaggaatgc ccatttgtgc aacgaacct gactccttcc | 1860 |
| tcaccctgac ttctccccct ccctacccgc gcgcaggcca agttgctgaa tcaatggagc | 1920 |
| cctcccaac ccgggcgttc cccagcgagg cttccttccc atcctcctga ccaccggggc | 1980 |
| ttttcgtgag ctcgtctctg atctcgcgca agagtgacac acaggtgttc aaagacgctt | 2040 |
| ctggggagtg agggaagcgg tttacgagtg acttggctgg agcctcaggg gcgggcactg | 2100 |
| gcacggaaca caccctgagg ccagccctgg ctgcccaggc ggagctgcct cttctcccgc | 2160 |
| ggacatgtac agagctcgag aagtactagt ggccacgtgg gccgtgcacc ttaagcttta | 2220 |
| gggtcgctgg agggggaccc cggttggaga gaggagcgga actcctggac aagccctgac | 2280 |
| aagccaagcc aaaggtccgc tccggcgcgg gtgggtgagt gcgcgccgcc ccgcgggggc | 2340 |
| ggggagagag cctgcagcct tcagaacaga tattgctcat tttctggcag ttctcagacg | 2400 |

-continued

```
taggaaataa gtcagcaccg aagcagtggt taagccggag ggctcggaag aacggcacct    2460
tttctttctc gaaaaagtta tatgggggct gaatgagctt ctggaggctt gtttaccgtt    2520
ttttattgtc acacagaaaa ggaaactgcc ttgtctccct tccggaatt ctctctttaa     2580 gactgtaagt cgctgcctga gtggtttcat tttgtttgt ttttctgccc ttctctttct     2640
tcttttgccc tttcttagct tgcactccca tggtgatttc tgcttggtct cctgctgggg   2700
ttggtggtac tcgttcccac cgcacagaac ccggcgccta ttattggcca agaaacttga    2760
gcagcctgtt ttgaaaagtc cctcgctcag aaatgccagc ttgcagatgg ctaatcaaag    2820
agacgtg                                                              2827

<210> SEQ ID NO 5
<211> LENGTH: 20
<212> TYPE: DNA
<213> ORGANISM: Homo Sapiens

<400> SEQUENCE: 5
ggacaagccc tgacaagcca                                                  20

<210> SEQ ID NO 6
<211> LENGTH: 20
<212> TYPE: DNA
<213> ORGANISM: Homo Sapiens

<400> SEQUENCE: 6
ggaaaagccc tgacaagcca                                                  20

<210> SEQ ID NO 7
<211> LENGTH: 20
<212> TYPE: DNA
<213> ORGANISM: Homo Sapiens

<400> SEQUENCE: 7
ggaaaagccc tgaaaagcca                                                  20

<210> SEQ ID NO 8
<211> LENGTH: 20
<212> TYPE: DNA
<213> ORGANISM: Homo Sapiens

<400> SEQUENCE: 8
ggaaaatccc tgaaaatcca                                                  20

<210> SEQ ID NO 9
<211> LENGTH: 20
<212> TYPE: DNA
<213> ORGANISM: Homo Sapiens

<400> SEQUENCE: 9
gcacaagccc tcacaagcca                                                  20

<210> SEQ ID NO 10
<211> LENGTH: 20
<212> TYPE: DNA
<213> ORGANISM: Homo Sapiens

<400> SEQUENCE: 10
ggacaagccc tgacaagcca                                                  20

<210> SEQ ID NO 11
<211> LENGTH: 20
```

<212> TYPE: DNA
<213> ORGANISM: Homo Sapiens

<400> SEQUENCE: 11
ggaaaatccc tgaaaatcca                                              20

<210> SEQ ID NO 12
<211> LENGTH: 20
<212> TYPE: DNA
<213> ORGANISM: Homo Sapiens

<400> SEQUENCE: 12
agagatgccc aaactgtttt                                              20

<210> SEQ ID NO 13
<211> LENGTH: 20
<212> TYPE: DNA
<213> ORGANISM: Homo Sapiens

<400> SEQUENCE: 13
agagattccc aaaatgtttt                                              20

<210> SEQ ID NO 14
<211> LENGTH: 20
<212> TYPE: DNA
<213> ORGANISM: Homo Sapiens

<400> SEQUENCE: 14
aatgttgctt aagcttttt                                               20

<210> SEQ ID NO 15
<211> LENGTH: 20
<212> TYPE: DNA
<213> ORGANISM: Homo Sapiens

<400> SEQUENCE: 15
aatgtttctt aagattttt                                               20

<210> SEQ ID NO 16
<211> LENGTH: 20
<212> TYPE: DNA
<213> ORGANISM: Homo Sapiens

<400> SEQUENCE: 16
aaactaccta agagctatct                                              20

<210> SEQ ID NO 17
<211> LENGTH: 20
<212> TYPE: DNA
<213> ORGANISM: Homo Sapiens

<400> SEQUENCE: 17
acaataccta agagctatct                                              20

<210> SEQ ID NO 18
<211> LENGTH: 40
<212> TYPE: DNA
<213> ORGANISM: Homo Sapiens

<400> SEQUENCE: 18
aataaccttt agagatgccc aaactgtttt ccccagaaca                        40

<210> SEQ ID NO 19

```
<211> LENGTH: 26
<212> TYPE: DNA
<213> ORGANISM: Homo Sapiens

<400> SEQUENCE: 19
aataaccttt agatctcccc agaaca                                    26

<210> SEQ ID NO 20
<211> LENGTH: 40
<212> TYPE: DNA
<213> ORGANISM: Homo Sapiens

<400> SEQUENCE: 20
catctttgcc aatgttgctt aagctttttt ggctacattt                     40

<210> SEQ ID NO 21
<211> LENGTH: 26
<212> TYPE: DNA
<213> ORGANISM: Homo Sapiens

<400> SEQUENCE: 21
catctttgcc actagtggctacattt                                     26

<210> SEQ ID NO 22
<211> LENGTH: 40
<212> TYPE: DNA
<213> ORGANISM: Homo Sapiens

<400> SEQUENCE: 22
aattcatgct aaactaccta agagctatct accgttccaa                     40

<210> SEQ ID NO 23
<211> LENGTH: 26
<212> TYPE: DNA
<213> ORGANISM: Homo Sapiens

<400> SEQUENCE: 23
aattcatgct atgcataccg ttccaa                                    26

<210> SEQ ID NO 24
<211> LENGTH: 20
<212> TYPE: DNA
<213> ORGANISM: Homo Sapiens

<400> SEQUENCE: 24
ggacaagccc tgacaagcca                                           20

<210> SEQ ID NO 25
<211> LENGTH: 20
<212> TYPE: DNA
<213> ORGANISM: Homo Sapiens

<400> SEQUENCE: 25
ggaaaatccc tgaaaatcca                                           20

<210> SEQ ID NO 26
<211> LENGTH: 40
<212> TYPE: DNA
<213> ORGANISM: Homo Sapiens

<400> SEQUENCE: 26
aataaccttt agagatgccc aaactgtttt ccccagaaca                     40

<210> SEQ ID NO 27
```

```
-continued

<211> LENGTH: 26
<212> TYPE: DNA
<213> ORGANISM: Homo Sapiens

<400> SEQUENCE: 27
aataaccttt agatctcccc agaaca                                          26

<210> SEQ ID NO 28
<211> LENGTH: 40
<212> TYPE: DNA
<213> ORGANISM: Homo Sapiens

<400> SEQUENCE: 28
catctttgcc aatgttgctt aagctttttt ggctacattt                           40

<210> SEQ ID NO 29
<211> LENGTH: 26
<212> TYPE: DNA
<213> ORGANISM: Homo Sapiens

<400> SEQUENCE: 29
catctttgcc actagtggct acattt                                          26

<210> SEQ ID NO 30
<211> LENGTH: 40
<212> TYPE: DNA
<213> ORGANISM: Homo Sapiens

<400> SEQUENCE: 30
aattcatgct aaactaccta agagctatct accgttccaa                           40

<210> SEQ ID NO 31
<211> LENGTH: 26
<212> TYPE: DNA
<213> ORGANISM: Homo Sapiens

<400> SEQUENCE: 31
aattcatgct atgcataccg ttccaa                                          26

<210> SEQ ID NO 32
<211> LENGTH: 266
<212> TYPE: DNA
<213> ORGANISM: Homo Sapiens

<400> SEQUENCE: 32
gatcccgctg ggcaggcggg gcagctccgg cgctcctcgg agaccactgc gctccacgtt     60
gaggtgggcg tgggggcgg acaggaattg aagcggaagt ctgggaagct ttagggtcgc     120
tggaggggga ccccggttgg agagaggagc ggaactcctg gacaagccct gacaagccaa    180
gccaaaggtc cgctccggcg cgggtgggtg agtgcgcgcc gccccgcggg ggcggggaga    240
gagcctgcag ccttcagaac agatat                                         266
```